(12) United States Patent
Gao et al.

(10) Patent No.: US 9,631,041 B2
(45) Date of Patent: *Apr. 25, 2017

(54) PH-SENSITIVE COMPOSITIONS FOR DELIVERY OF BETA LAPACHONE AND METHODS OF USE

(75) Inventors: Jinming Gao, Plano, TX (US); David Boothman, Dallas, TX (US); Yinjian Zhou, Beijing (CN); Erik Bey, Morgantown, WV (US)

(73) Assignee: The Board of Regents of the University of Texas System, Austin, TX (US)

( * ) Notice: Subject to any disclaimer, the term of this patent is extended or adjusted under 35 U.S.C. 154(b) by 745 days.

This patent is subject to a terminal disclaimer.

(21) Appl. No.: 13/825,524

(22) PCT Filed: Aug. 11, 2011

(86) PCT No.: PCT/US2011/047497
§ 371 (c)(1),
(2), (4) Date: Aug. 26, 2013

(87) PCT Pub. No.: WO2012/039855
PCT Pub. Date: Mar. 29, 2012

(65) Prior Publication Data
US 2013/0331426 A1 Dec. 12, 2013

Related U.S. Application Data

(60) Provisional application No. 61/385,422, filed on Sep. 22, 2010, provisional application No. 61/470,441, filed on Mar. 31, 2011, provisional application No. 61/471,054, filed on Apr. 1, 2011.

(51) Int. Cl.
| | | |
|---|---|---|
| C07D 311/92 | (2006.01) |
| C08F 293/00 | (2006.01) |
| A61K 9/127 | (2006.01) |
| A61K 47/48 | (2006.01) |
| A61K 9/50 | (2006.01) |
| A61K 31/337 | (2006.01) |
| A61K 31/704 | (2006.01) |
| A61K 49/00 | (2006.01) |
| A61K 31/352 | (2006.01) |
| A61K 9/107 | (2006.01) |
| C08F 220/34 | (2006.01) |

(52) U.S. Cl.
CPC ........ *C08F 293/005* (2013.01); *A61K 9/1075* (2013.01); *A61K 9/1273* (2013.01); *A61K 9/5031* (2013.01); *A61K 31/337* (2013.01); *A61K 31/352* (2013.01); *A61K 31/704* (2013.01); *A61K 47/48176* (2013.01); *A61K 47/48215* (2013.01); *A61K 47/48238* (2013.01); *A61K 49/0032* (2013.01); *A61K 49/0054* (2013.01); *A61K 49/0056* (2013.01); *A61K 49/0082* (2013.01); *C07D 311/92* (2013.01); *C08F 220/34* (2013.01); *C08F 2438/01* (2013.01)

(58) Field of Classification Search
CPC .................................................... C07D 311/92
See application file for complete search history.

(56) References Cited

U.S. PATENT DOCUMENTS

| | | | |
|---|---|---|---|
| 2006/0034796 A1* | 2/2006 | Ashwell | A61K 31/785 424/78.27 |
| 2008/0081075 A1 | 4/2008 | Hsiue et al. | |
| 2008/0248097 A1* | 10/2008 | Kwon | A61K 9/1075 424/450 |

FOREIGN PATENT DOCUMENTS

| | | |
|---|---|---|
| WO | WO 03/074026 | 9/2003 |
| WO | WO 2009/138473 | 11/2009 |
| WO | WO 2012/039741 | 3/2012 |

OTHER PUBLICATIONS

Bae et al. Advanced Drug Delivery Reviews 2009, 61, 768-784.*
Pinto et al. Molecules 2009, 14, 4570-4590.*
Luo et al. Cell, 2009, 136, pp. 823-837.*
Alani et al., "Polymeric micelles for the pH-dependent controlled, continuous low dose release of paclitaxel," *Biomaterials*, 31:1765-772, 2010.
Albertazzi et al., "Delivery and subcellular targeting of dendrimer-based fluorescent pH sensors in living cells," *J Am Chem Soc.*, 132:18158-67, 2010.
Almutairi et al., "Biodegradable pH-sensing dendritic nanoprobes for near-infrared fluorescence lifetime and intensity imaging," *J Am Chem Soc.*, 130:444-5, 2008.
Bae et al., "Design of environment-sensitive supramolecular assemblies for intracellular drug delivery: polymeric micelles that are responsive to intracellular pH change," *Angew Chem Int Ed Engl.*, 42:4640-4643, 2003.
Bae et al., "Multifunctional polymeric micelles with folate-mediated cancer cell targeting and pH-triggered drug releasing properties for active intracellular drug delivery," *Mol BioSyst.*, 1:242-250, 2005.

(Continued)

*Primary Examiner* — Matthew Coughlin
(74) *Attorney, Agent, or Firm* — Parker Highlander PLLC

(57) ABSTRACT

Disclosed herein are compounds comprising a polymer conjugated with a pH-sensitive prodrug of beta-lapachone, wherein the compound is capable of forming a micelle, and wherein the pH-sensitive prodrug comprises a pH-sensitive linker selected from the group consisting of: an aryl imine and an aliphatic imine. Also provided are micelles comprised of such polymer-prodrug conjugates. Further provided are methods for treating cancer with the micelles.

29 Claims, 8 Drawing Sheets

(56) References Cited

OTHER PUBLICATIONS

Bae et al., "Preparation and Biological Characterization of Polymeric Micelle Drug Carriers with Intracellular pH-Triggered Drug Release Property: Tumor Permeability, Controlled Subcellular Drug Distribution, and Enhanced in Vivo Antitumor Efficacy," *Bioconjug Chem.*, 16:122-30, 2005.
Benjaminsen et al., "Evaluating nanoparticle sensor design for intracellular pH measurements," *ACS Nano*, 5:5864-73, 2011.
Blanco et al., "β-Lapachone-containing PEG-PLA Polymer Micelles as Novel Nanotherapeutics against NQO1-Overexpressing Tumor Cells," *J Control Release*, 122(3):365-374, 2007.
Braunecker et al., "Controlled/living radical polymerization: Features, developments, and perspectives," *Progress in Polymer Science*, 32(1):93-146, 2007.
Bütün et al., "Synthesis and aqueous solution properties of near-monodisperse tertiary amine methacrylate homopolymers and diblock copolymers," *Polymer*, 42:5993-6008, 2001.
Casey et al., "Sensors and regulators of intracellular pH," *Nat Rev Mol Cell Biol.*, 11:50- 61, 2010.
Chenna et al., "Preparation and cytotoxicity toward cancer cells of mono(arylimino) derivatives of beta-lapachone," *J Med Chem.*, 44:2486-2489, 2001.
De Silva et al., "Signaling recognition events with fluorescent sensors and switches," *Chem Rev.*, 97:1515-1566, 1997.
Diaz-Fernandez et al., "Micelles for the self-assembly of "off-on-off" fluorescent sensors for pH windows," *Chemistry—A European Journal*, 12(3):921-930, 2006.
Ghosh et al., "Simultaneous and reversible functionalization of copolymers for biological applications," *Macromolecules*, 39:5595-5597, 2006.
Giacomelli et al., "Specific interactions improve the loading capacity of block copolymer micelles in aqueous media," *Langmuir*, 23:6947-6955, 2007.
Gijs et al., "Thiol chemistry on well-defined synthetic polypeptides," *Chem Comm.*, 24:3612-3614, 2009.
Griset et al., "Expansile nanoparticles: synthesis, characterization, and in vivo efficacy of an acid-responsive polymeric drug delivery system," *J Am Chem Soc.*, 131:2469-2471, 2009.
Han et al., "Fluorescent indicators for intracellular pH," *Chem Rev.*, 110(5):2709-28, 2010.
Heffernan et al., "Polyketal nanoparticles: a new pH-sensitive biodegradable drug delivery vehicle," *Bioconjugate Chem.*, 16:1340-1342, 2005.
Hu et al., "Synthesis and pH-dependent micellization of 2-(diisopropylamino)ethyl methacrylate based amphiphilic diblock copolymers via RAFT polymerization," *Polymer*, 48:3437-3443, 2007.
Izumi et al., "Cellular pH regulators: potentially promising molecular targets for cancer chemotherapy," *Cancer Treat Rev.*, 29(6):541-9, 2003.
Jung et al., "pH-sensitive polymer nanospheres for use as a potential drug delivery vehicle," *Biomacromolecules*, 8:3401-7, 2007.
Kato et al., "Polymerization of methyl methacrylate with the carbon tetrachloride/dichlorotris-(triphenylphosphine)ruthedum(II)/methylaluminum bis(2,6-di-tertbutylphenoxide) initiating system: possibility of living radical polymerization," *Macromolecules*, 28:1721-1723, 1995.
Khemtong et al., "In vivo off-resonance saturation magnetic resonance imaging of $\alpha_v\beta_3$-targeted superparamagnetic nanoparticles," *Cancer Res.*, 69:1651-1658, 2009.
Kim et al., "Doxorubicin loaded pH-sensitive micelle: antitumoral efficacy against ovarian A2780/DOXR tumor," *Pharm Res.*, 25:2074-82, 2008.
Kim et al., "Multicenter phase II trial of Genexol-PM, a novel Cremophor-free, polymeric micelle formulation of paclitaxel, with cisplatin in patients with advanced non-small-cell lung cancer," *Ann Oncol.*, 18(12):2009-14, 2007.
Kobayashi et al., "New strategies for fluorescent probe design in medical diagnostic imaging," *Chem Rev.*, 110(5):2620-40, 2010.
Kobayashi et al., "Target-cancer-cell-specific activatable fluorescence imaging probes: rational design and in vivo applications,"*Acc Chem Res.*, 44(2):83-90, 2011.
Lakowicz, "Chapter 13. Energy Transfer," *Principles of Fluorescence Spectroscopy*, $3^{rd}$ ed., New York City: Springer, 2006. 443-475. Print.
Lee et al., "Activatable imaging probes with amplified fluorescent signals," *Chem Commun.*, 36:4250-60, 2008.
Lee et al., "Doxorubicin loaded pH-sensitive polymeric micelles for reversal of resistant MCF-7 tumor," *J Control Release*, 103:405-18, 2005.
Lee et al., "Poly(L-histidine)-PEG block copolymer micelles and pH-induced destabilization," *J Control Release*, 90:363-74, 2003.
Li et al., "pH-activated near-infrared fluorescence nanoprobe imaging tumors by sensing the acidic microenvironment," *Adv Funct Mater.*, 20:2222-2230, 2010.
Licciardi et al., "Synthesis of novel folic acid-functionalized biocompatible block copolymers by atom transfer radical polymerization for gene delivery and encapsulation of hydrophobic drugs," *Biomacromolecules*, 6:1085-1096, 2005.
Lopalco et al., "Catch and release microwave mediated synthesis of cyanine dyes," *Org Biomol Chem.*, 7:856-859, 2009.
Lovell et al., "Activatable photosensitizers for imaging and therapy," *Chem Rev.*, 110(5):2839-57, 2010.
Ma et al., "Well-defined biocompatible block copolymers via atom transfer radical polymerization of 2-methacryloyloxyethyl phosphorylcholine in protic media," *Macromolecules*, 36(10):3475-3484, 2003.
Marconescu, "Targeting nanoparticles to tumor vasculature," PhD Thesis, UT Southwestern Medical Center, Dallas, 2008.
Maxfield et al., "Endocytic recycling," *Nat Rev Mol Cell Biol.*, 5(2)121-32, 2004.
McAllister et al., "Polymeric nanogels produced via inverse microemulsion polymerization as potential gene and antisense delivery agents," *J Am Chem Soc.*, 124:15198-15207, 2002.
Moad et al., "Living radical polymerization by the RAFT process," *Australian Journal of Chemistry*, 58(6):379-410, 2005.
Modi et al., "A DNA nanomachine that maps spatial and temporal pH changes inside living cells," *Nat Nanotech.*, 4:325-330, 2009.
Nakanishi et al., "Development of the polymer micelle carrier system for doxorubicin," *J Control Release*, 74:295-302, 2001.
Nasongkla et al., "Multifunctional polymeric micelles as cancer-targeted, MRI-ultrasensitive drug delivery systems," *Nano Lett.*, 6:2427-2430, 2006.
Nishi et al., "The vacuolar (H+)-ATPases—nature's most versatile proton pumps," *Nat Rev Mol Cell Biol.*, 3(2):94-103, 2002.
Reinicke et al., "Develoment of beta-Lapachone prodrugs for therapy agains human cancer cells with elevated NAD(P)H:Quinone Oxidoreductase 1 levels," *Clin Cancer Res.*, 11:3055-3064, 2005.
Seshadri et al., "The delivery of superoxide dismutase encapsulated in polyketal microparticles to rat myocardium and protection from myocardial ischemia-reperfusion injury," *Biomaterials*, 31:1372-1379, 2010.
Srikun et al., "A dendrimer-based platform for simultaneous dual fluorescence imaging of hydrogen peroxide and pH gradients produced in living cells," *Chemical Science*, 2:1156-1165, 2011.
Sun et al., "Bright fluorescent nanoparticles for developing potential optical imaging contrast agents," *Nanoscale*, 2:548-558, 2010.
Sutton et al., "Doxorubicin and beta-lapachone release and interaction with micellar core materials: experiment and modeling," *Exp Biol Med.*, 232(8):1090-9, 2007.
Sutton et al., "Functionalized micellar systems for cancer targeted drug delivery," *Pharmaceutical Research*, 24(6):1029-1049, 2007.
Sutton, "Chapter 5: Hydrophobic prodrug strategy for the creation of polymeric micelles with pHsensitive release of beta-lapachone," *pH Sensitive RNA and Drug Delivery Systems—Ph.D. Dissertation*, Case Western Reserve University, Cleveland, 2007. 174-206.
Sy et al., "Surface functionalization of polyketal microparticles with nitrilotriacetic acid-nickel complexes for efficient protein capture and delivery," *Biomaterials*, 31:4987-4994, 2010.

(56) References Cited

OTHER PUBLICATIONS

Tsarevsky et al., "'Green' atom transfer radical polymerization: from process design to preparation of well-defined environmentally friendly polymeric materials," *Chem Rev.*, 107(6):2270-99, 2007.
Uchiyama et al., "Multiplexing sensory molecules map protons near micellar membranes," *Angew Chem Int Ed Engl.*, 47(25):4667-9, 2008.
Ueno et al., "Fluorescent probes for sensing and imaging," *Nat methods*, 8(8):642-5, 2011.
Urano et al., "Selective molecular imaging of viable cancer cells with pH-activatable fluorescence probes," *Nat Med.*, 15:104-109, 2009.
Vetvicka et al., "Biological evaluation of polymeric micelles with covalently bound doxorubicin," *Bioconjug Chem.*, 20:2090-2097, 2009.
Wang et al., "Controlled living radical polymerization—atom-transfer radical polymerization in the presence of transition-metal complexes," *J Am. Chem Soc.*, 117:5614-5615, 1995.
Webb et al., "Dysregulated pH: a perfect storm for cancer progression," *Nat Rev Cancer*, 11(9):671-7, 2011.
Ye et al., "Novel near-infrared fluorescent integrin-targeted DFO analogue," *Bioconjug Chem.*, 19:225-234, 2007.
Yezhelyev et al., "Proton-sponge coated quantum dots for siRNA delivery and intracellular imaging,"*J Am Chem Soc.*, 130(28):9006-12, 2008.
Yu et al., "Overcoming endosomal barrier by amphotericin B-loaded dual pH-responsive PDMA-b-PDPA micelleplexes for siRNA delivery," *ACS Nano*, 5(11):9246-55, 2011.
Zhang et al., "Creating new fluorescent probes for cell biology," *Nat Rev Mol Cell Biol.*, 3(12):906-18, 2002.
Zhou et al., "Tunable, ultra-sensitive pH responsive nanoparticles targeting specific endocytic organelles in living cells," *Angew Chem Int Ed Engl.*, 50:6109-6114, 2011.
PCT International Preliminary Report on Patentability issued in International application No. PCT/US2011/001418, dated Apr. 4, 2013.
PCT International Preliminary Report on Patentability issued in International application No. PCT/US2011/047497, dated Apr. 4, 2013.
PCT International Search Report and Written Opinion issued in International application No. PCT/US2011/001418, dated Dec. 2, 2011.
PCT International Search Report and Written Opinion issued in International application No. PCT/US2011/047497, dated Oct. 21, 2011.
PCT Invitation to Pay Additional Fees issued in International application No. PCT/US2013/035050, dated Jul. 11, 2013.
Nonprovisional U.S. Appl. No. 13/825,518 entitled "Novel Block Copolymer and Micelle Compositions and Methods of Use Thereof," submitted to the United States Patent Office on Mar. 21, 2013.
Nonprovisional U.S. Appl. No. 13/827,197 entitled "Multicolored pH-Activatable Fluorescence Nanoplatform," submitted to the United States Patent Office on Mar. 14, 2013.

\* cited by examiner

US 9,631,041 B2

PH-SENSITIVE COMPOSITIONS FOR DELIVERY OF BETA LAPACHONE AND METHODS OF USE

CROSS REFERENCE TO RELATED APPLICATIONS

This application is a national phase application under 35 U.S.C. §371 of International Application No. PCT/US2011/047497, filed Aug. 11, 2011, which claims the benefit under 35 U.S.C. §119(e) of U.S. Provisional Application Ser. Nos. 61/470,441 filed Mar. 31, 2011, 61/471,054 filed on Apr. 1, 2011, and 61/385,422 filed on Sep. 22, 2010. The entire content of each of the above referenced disclosures is specifically incorporated herein by reference.

STATEMENT AS TO FEDERALLY SPONSORED RESEARCH

This invention was made with government support under Grant Numbers R01CA122994, R01CA129011, R01 CA102792 awarded by the National Institutes of Health. The government has certain rights in the invention.

BACKGROUND

β-Lapachone (β-lap) is a natural product isolated from the lapacho tree in South America. Beta lapachone is a potent cytotoxic anticancer agent with antitumor activity against a variety of human cancer cells, including drug resistant cell lines. Recent studies uncovering its unique mechanism of action have raised considerable interests for the clinical evaluation of this agent. β-Lap kills tumor cells containing NADP(H):quinone oxidoreductase 1 (NQO1), an enzyme overexpressed in a number of tumors, including breast, colon, and lung cancers (Bentle, M. S., Reinicke, K. E., Dong, Y., Bey, E. A., and Boothman, D. A. (2007) Nonhomologous End Joining Is Essential for Cellular Resistance to the Novel Antitumor Agent β-Lapachone. Can. Res. 67, 6936-6945), prostate (Dong, Y., Chin, S. F., Blanco, E., Bey, E. A., Kabbani, W., Xie, X. J., Bornmann, W. G., Boothman, D. A., and Gao, J. (2009) Intratumoral Delivery of -Lapachone via Polymer Implants for Prostate Cancer Therapy. Clin. Can. Res. 15, 131-139), pancreas (Ough, M., Lewis, A., Bey, E. A., Gao, J., Ritchie, J. M., Bornmann, W., Boothman, D. A., Oberley, L. W., and Cullen, J. J. (2005) Efficacy of beta-lapachone in pancreatic cancer treatment: exploiting the novel, therapeutic target NQO1. Can. Bio. Ther. 4, 95-102), and non-small cell lung cancers (NSCLC) (Bey, E. A., Bentle, M. S., Reinicke, K. E., Dong, Y., Yang, C. R., Girard, L., Minna, J. D., Bornmann, W. G., Gao, J., and Boothman, D. A. (2007) An NQO1- and PARP-1-mediated cell death pathway induced in non-small-cell lung cancer cells by beta-lapachone. Proc. Natl. Acad. Sci. USA 104, 11832-11837).

Upon NQO1 bioactivation, β-lap undergoes a futile cycle resulting in the rapid formation of reactive oxygen species (ROS) and depletion of NAD(P)H. Each mole of β-lap can produce 120 moles of $H_2O_2$ and other ROS, which causes DNA single-strand breaks, hyper-activation of poly(ADP-ribose) of polymerase-1, loss of NAD+ and ATP, and irreversible cell death (Tagliarino, C., Pink, J. J., Dubyak, G. R., Nieminen, A. L., and Boothman, D. A. (2001) Calcium is a key signaling molecule in beta-lapachone-mediated cell death. J. Biol. Chem. 276, 19150-19159). Cell death by β-lap is independent of p53, cell cycle and Rb status, and no drug resistance has been found. At optimal concentrations and duration of exposure to cells, beta lap causes DNA damage, inhibits DNA repair and induces programmed cell death.

Despite the unique mechanism of action, selectivity and potency, preclinical and clinical evaluations of β-lap are currently limited. Free β-lap has a low aqueous solubility of 0.038 mg/ml, which limits direct injection in patients. Hydroxylpropyl β-cyclodextrin has been used to effectively solubilize β-lap by the formation of inclusion complex. The low binding affinity (binding constant=$1.1\times10^3 M^{-1}$) (Wang, F., Blanco, E., Ai, H., Boothman, D. A., and Gao, J. (2006) Modulating β-lapachone release from polymer millirods through cyclodextrin complexation. J. Pharm. Sci. 95, 2309-2319), however, resulted in the rapid dissociation of the complex, fast renal clearance and short half-life (0.4 hour) in blood, far shorter than the minimally required duration of drug exposure needed to achieve cytotoxicity. In addition, hemolysis and hemoglobinemia were found as the major side effects, causing the withdrawal of the complex (ARQ501) from clinical trials. A better delivery strategy for β-lap is greatly needed.

Polymeric micelles are supramolecular core-shell nanoparticles self-assembled from amphiphilic block copolymers. Micelle formations containing a drug have been described. Kim, D. W., Kim, S. Y., Kim, H. K., Kim, S. W., Shin, S. W., Kim, J. S., Park, K., Lee, M. Y., and Heo, D. S. (2007) Multicenter phase II trial of Genexol-PM, a novel Cremophor-free, polymeric micelle formulation of paclitaxel, with cisplatin in patients with advanced non-small-cell lung cancer. Ann Oncol 18, 2009-14).

The lower pH of tumor extracellular and tumor cell late endosomal/lysosomal (pH 4.0-5.0) compared to normal tissue cells and bloodstream (Vaupel, P., Kallinowski, F., and Okunieff, P. (1989) Blood flow, oxygen and nutrient supply, and metabolic microenvironment of human tumors: a review. Can. Res. 49, 6449-65; Ulbrich, K., and Subr, V. (2004) Polymeric anticancer drugs with pH-controlled activation. Adv Drug Deliv Rev 56, 1023-50; Ganta, S., Devalapally, H., Shahiwala, A., and Amiji, M. (2008) A review of stimuli-responsive nanocarriers for drug and gene delivery. J. Controlled. Release 126, 187-204) can facilitate pH responsive delivery of anticancer drugs by polymeric micelles; the polymeric micelles may keep integrity in the bloodstream pH but release their contents when exposed to tumor extracellular pH or late endosome/lysosome pH. However, the release of contents will be retarded or hindered (Griset, A. P., Walpole, J., Liu, R., Gaffey, A., Colson, Y. L., and Grinstaff, M. W. (2009) Expansile nanoparticles: synthesis, characterization, and in vivo efficacy of an acid-responsive polymeric drug delivery system. J. Am. Chem. Soc. 131, 2469-2471) if micelle cores are not sensitive enough to outer pH stimuli.

One type of pH sensitive polymeric micelles are polymer chains with ionizable groups which act as hydrophilic or hydrophobic parts of a polymer at various water pH. The polymer is soluble when it is ionized, but it is insoluble when it is deionized, which causes a reversible soluble-insoluble transition to occur as the hydrophobicity of the polymer changes. An acidic group such as a carboxyl group becomes ionized at pH values above the pKa and deionized at pH values below the pKa, whereas a basic group such as an amine becomes deionized at pH values below the pKb and ionized at pH values above pKb.

Various micelle systems have been described. See e.g.: Sutton, D., Nasongkla, N., Blanco, E., and Gao, J. (2007) Functionalized micellar systems for cancer targeted drug delivery. Pharm. Res. 24, 1029-1046;

Bae, Y., Jang, W.-D., Nishiyama, N., Fukushima, S., and Kataoka, K. (2005) Multifunctional polymeric micelles with folate-mediated cancer cell targeting and pH-triggered drug releasing properties for active intracellular drug delivery. Mol Biosyst 1, 242-50;

Bae, Y., Nishiyama, N., Fukushima, S., Koyama, Yasuhiro, M., and Kataoka, K. (2005) Preparation and biological characterization of polymeric micelle drug carriers with intracellular pH-triggered drug release property: tumor permeability, controlled subcellular drug distribution, and enhanced in vivo antitumor efficacy. Bioconjug Chem 16, 122-30;

Vetvicka, D., Hruby, M., Hovorka, O., Etrych, T., Vetrik, M., Kovar, L., Kovar, M., Ulbrich, K., and Rihova, B. (2009) Biological evaluation of polymeric micelles with covalently bound doxorubicin. Bioconjugate Chem. 20, 2090-2097;

Jung, J., Lee, I.-H., Lee, E., Park, J., and Jon, S. (2007) pH-sensitive polymer nanospheres for use as a potential drug delivery vehicle. Biomacromolecules 8, 3401-7;

Lee, E. S., Shin, H. J., Na, K., and Bae, Y. H. (2003) Poly(L-histidine)-PEG block copolymer micelles and pH-induced destabilization. J Control Release 90, 363-74;

Lee, E. S., Na, K., and Bae, Y. H. (2005) Doxorubicin loaded pH-sensitive polymeric micelles for reversal of resistant MCF-7 tumor. J Control Release 103, 405-18;

Kim, D., Lee, E. S., Park, K., Kwon, I. C., and Bae, Y. H. (2008) Doxorubicin loaded pH-sensitive micelle: antitumoral efficacy against ovarian A2780/DOXR tumor. Pharm. Res. 25, 2074-82;

Jung, J., Lee, I.-H., Lee, E., Park, J., and Jon, S. (2007) pH-sensitive polymer nanospheres for use as a potential drug delivery vehicle. Biomacromolecules 8, 3401-7.

Methacrylate polymers are described in: Butun, V., Armes, S. P., and Billingham, N. C. (2001) Synthesis and aqueous solution properties of near-monodisperse tertiary amine methacrylate homopolymers and diblock copolymers. Polymer 42, 5993-6008.

Acylhydrazone and ketal linkers have been reported. See, e.g.:

T. Nakanishi et al. (2001); Development of the polymer micelle carrier system for doxorubicin. J. Controlled. Release 74, 295-302;

Bae, Y., Fukushima, S., Harada, A., and Kataoka, K. (2003) Design of environment-sensitive supramolecular assemblies for intracellular drug delivery: polymeric micelles that are responsive to intracellular pH change. Angew. Chem. Int. Ed. Engl. 42, 4640-4643;

Alani, A. W. G., Bae, Y., Rao, D. A., and Kwon, G. S. (2010) Polymeric micelles for the pH-dependent controlled, continuous low dose release of paclitaxel. Biomaterials 31, 1765-1772;

Griset, A. P., Walpole, J., Liu, R., Gaffey, A., Colson, Y. L., and Grinstaff, M. W. (2009) Expansile nanoparticles: synthesis, characterization, and in vivo efficacy of an acid-responsive polymeric drug delivery system. J. Am. Chem. Soc. 131, 2469-2471.

Sy, J. C., Phelps, E. A., Garcia, A. J., Murthy, N., and Davis, M. E. (2010) Surface functionalization of polyketal microparticles with nitrilotriacetic acid-nickel complexes for efficient protein capture and delivery. Biomaterials 31, 4987-4994;

Seshadri, G., Sy, J. C., Brown, M., Dikalov, S., Yang, S. C., Murthy, N., and Davis, M. E. (2010) The delivery of superoxide dismutase encapsulated in polyketal microparticles to rat myocardium and protection from myocardial ischemia-reperfusion injury. Biomaterials 31, 1372-1379; and Heffernan, M. J., and Murthy, N. (2005) Polyketal nanoparticles: a new pH-sensitive biodegradable drug delivery vehicle. Bioconjugate Chem. 16, 1340-1342).

What is needed are improved compositions and methods for delivery of β-lap.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention.

SUMMARY OF THE INVENTION

In one aspect of the invention is a compound comprising a polymer conjugated with a pH-sensitive prodrug of beta-lapachone, wherein the compound is capable of forming a micelle, and wherein the pH-sensitive prodrug comprises a pH-sensitive linker selected from the group consisting of: an aryl imine and an aliphatic imine. In some embodiments, the pH-sensitive linker is an aryl imine. In some embodiments, the aryl imine is a phenyl imine. In some embodiments, the phenyl comprises a substitutent. In some embodiments, the substituent is at the para position. In some embodiments, the substituent is —OH, —NH$_2$, —SH, or maleimide

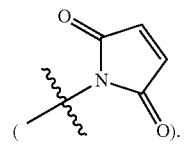

In some embodiments, the substituent is maleimide

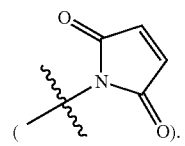

In some embodiments, the pH-sensitive linker is an aliphatic imine. In some embodiments, the Ca of the aliphatic imine comprises at least one substitutent. In some embodiments, the Ca of the aliphatic imine comprises two substitutents. In some embodiments, the substitutents are both methyl. In some embodiments, the pH-sensitive prodrug is selected from the group consisting of:

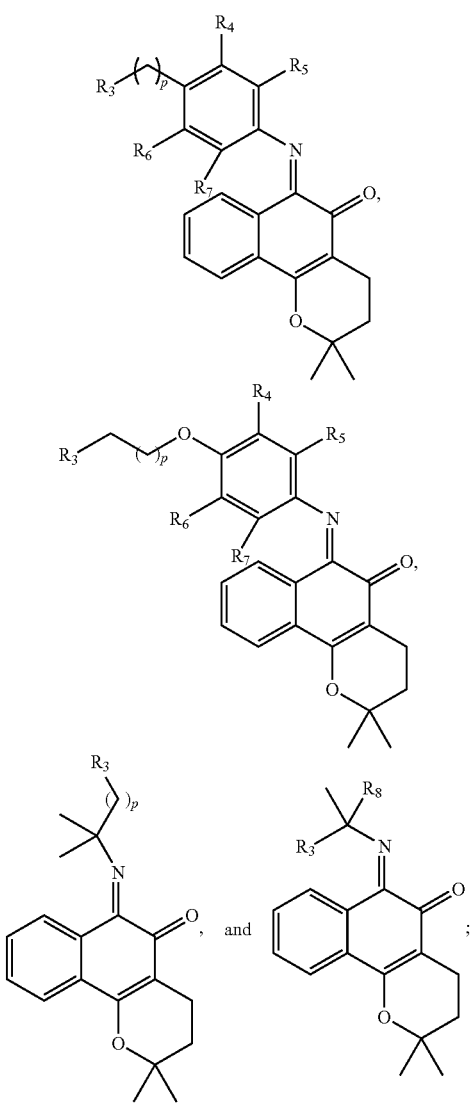

wherein $R_8$ is a side chain of a D or L amino acid other than —H; $R_3$ is —NH$_2$, —OH, —SH, or

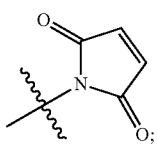

each of $R_4$, $R_5$, $R_6$, and $R_7$ is independently —H, —X, —OCH$_3$, or —CH$_3$; X is a halogen; and p is an integer between 0 and 20. In some embodiments, $R_8$ is —CH$_3$. In some embodiments, $R_3$ is

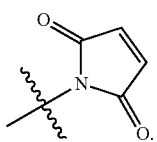 [SMILES: *N1C(=O)C=CC1=O]

In some embodiments, $R_3$ is —OH. In some embodiments, each of $R_4$, $R_5$, $R_6$, and $R_7$ is H. In some embodiments, X is Cl, Br, I, or F. In some embodiments, p is 0-6. In some embodiments, the prodrug is linked to the polymer by a bond selected from the group consisting of: an ester bond, an amide bond, a disulfide bond, or a thioether bond. In some embodiments, the polymer comprises a block copolymer comprising a hydrophilic polymer segment and a hydrophobic polymer segment. In some embodiments, the hydrophobic polymer segment comprises a poly(L-cysteine) block. In some embodiments, the poly(L-cysteine) block comprises about 5 to about 50 cysteine residues. In some embodiments, the poly(L-cysteine) block comprises about 20 to about 50 cysteine residues. In some embodiments, the poly(L-cysteine) block comprises about 30 to about 40 cysteine residues. In some embodiments, the prodrug is conjugated to one or more cysteines residues. In some embodiments, the prodrug is conjugated to each cysteine residue. In some embodiments, the hydrophilic segment comprises polyethylene oxide (PEO). In some embodiments, the PEO is about 2 kD to about 20 kD in size. In some embodiments, the PEO is about 2 kD to about 10 kD in size. In some embodiments, the PEO is about 4 kD to about 6 kD in size. In some embodiments, the PEO is about 5 kD in size. In some embodiments, the compound is capable of forming a pH-sensitive micelle. In some embodiments, the polymer comprises a pH responsive segment. In some embodiments, the hydrophobic polymer segment is the pH responsive segment. In some embodiments, the hydrophilic segment comprises polyethylene oxide (PEO). In some embodiments, the compound comprises a block copolymer comprising a hydrophilic polymer segment and a hydrophobic polymer segment, wherein the hydrophilic polymer segment comprises a polymer selected from the group consisting of: poly(ethylene oxide) (PEO), poly(methacrylate phosphatidyl choline) (MPC), and polyvinylpyrrolidone (PVP), wherein the hydrophobic polymer segment comprises:

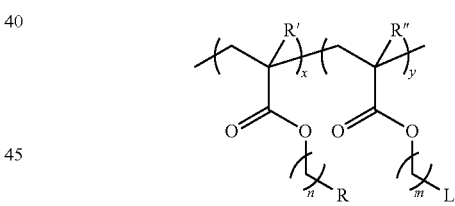

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, wherein x is about 10 to about 50 in total, wherein L is the prodrug conjugated to the polymer by a linker moiety, wherein y is 1 to about 30, wherein R'' is —H or —CH$_3$; wherein m is 1 to about 10; and wherein the moieties comprising R and the moieties comprising L may be arranged in any order. In some embodiments, the hydrophilic polymer segment comprises PEO. In some embodiments, n is 1 to 4. In some embodiments, n is 2. In some embodiments, R' is —CH$_3$. In some embodiments, R' is —H. In some embodiments, x is about 10 to about 30 in total. In some embodiments, x is about 10 to about 20 in total. In some embodiments, x is about 15 in total. In some embodiments, R$^1$ and R$^2$ are each straight or branched alkyl. In some embodiments, R$^1$ and R$^2$ join to form a ring. In some embodiments, R$^1$ and R$^2$ are the same.

In some embodiments, $R^1$ and $R^2$ are different. In some embodiments, $R^1$ and $R^2$ each have 3 to 8 carbons. In some embodiments, $R^1$ and $R^2$ together form a ring having 5 to 10 carbons. In some embodiments, $R^1$ and $R^2$ are propyl. In some embodiments, propyl is iso-propyl. In some embodiments, $R^1$ and $R^2$ are butyl. In some embodiments, butyl is n-butyl. In some embodiments, $R^1$ and $R^2$ together are —(CH$_2$)$_5$—. In some embodiments, $R^1$ and $R^2$ together are —(CH$_2$)$_6$—. In some embodiments, R" is —CH$_3$. In some embodiments, R" is —H. In some embodiments, m is 1 to 4. In some embodiments, m is 2. In some embodiments, the linker in L is a thioether. In some embodiments, y is about 3-10. In some embodiments, y is about 10-30. In some embodiments, y is about 3. In some embodiments, the compound comprises a compound of Formula I:

(Formula I)

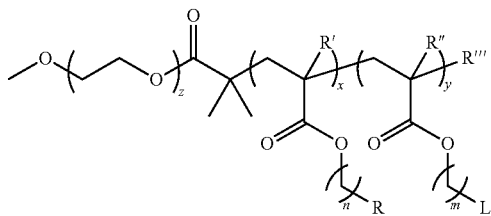

wherein z is such that the PEO is about 2 kD to about 20 kD in size, wherein R''' is any suitable moiety, and
wherein the following portion of the structure:

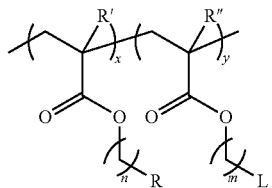

may be arranged in any order. In some embodiments, the PEO is about 2 kD to about 10 kD in size. In some embodiments, the PEO is about 4 kD to about 6 kD in size. In some embodiments, the PEO is about 5 kD in size. In some embodiments, z is about 114. In some embodiments, R''' is an end group resulting from a polymerization reaction. In some embodiments, R''' is Br. In some embodiments, R''' is thiolate. In some embodiments, R''' is a thioester. In some embodiments, the following portion of the structure:

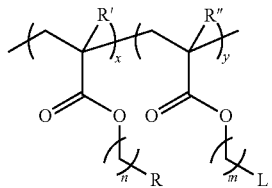

is randomized. In some embodiments, the compound forms a pH-sensitive micelle.

In another aspect of the invention is a composition comprising a pH-sensitive micelle, wherein the pH-sensitive micelle comprises a compound as described herein. In some embodiments, the micelle has a pH transition range of less than about 1 pH unit. In some embodiments, the micelle has a pH transition range of less than about 0.5 pH unit. In some embodiments, the micelle has a pH transition value of about 5 to about 8. In some embodiments, the micelle has a pH transition value of about 5 to about 6. In some embodiments, the micelle has a pH transition value of about 6 to about 7. In some embodiments, the micelle has a pH transition value of about 7 to about 8. In some embodiments, the micelle has a pH transition value of about 6.3 to about 6.9. In some embodiments, the micelle has a pH transition value of about 5.0 to about 6.2. In some embodiments, the micelle has a pH transition value of about 5.9 to about 6.2. In some embodiments, the micelle has a pH transition value of about 5.9 to about 6.5. In some embodiments, the micelle has a pH transition value of about 5.0 to about 5.5. In some embodiments, the micelle is stable at a neutral pH and releases beta-lapachone at a physiologically acidic pH.

In another aspect of the invention is a composition comprising a micelle as described herein and a pharmaceutically acceptable carrier.

In another aspect of the invention is a method for treating cancer in an individual in need thereof, comprising administration of an effective amount of a composition as described herein. In some embodiments, the cancer comprises a solid tumor.

Disclosed herein, in certain embodiments, are compositions comprising biocompatible polymeric prodrug micelles for delivering an encapsulated therapeutic agent, such as beta-lapachone, for cancer therapy. The formulations are stable at neutral pH, release beta-lap at acidic pHs (e.g. physiologically acidic pH such as the extracellular environment of tumors, early endosomes, late endosome, and lysosome), which may improve drug specificity and bioavailability in cancer cells. Further, the formulations may result in useful drug solubility, drug yield, shelf life, plasma stability and plasma circulation time. The formulations also may result in improved loading density of beta-lap, improved safety with no hemolysis, enhanced drug delivery into tumor cells, improved drug tissue distribution at tumor tissue and/or significantly enhanced cytotoxicity.

Disclosed herein, in certain embodiments, is a biocompatible polymeric prodrug micelle for delivering an encapsulated therapeutic agent. In some embodiments, the therapeutic agent is beta-lapachone. In some embodiments, the micelle formulation is stable at a neutral pH (e.g. a physiologically neutral pH) and releases beta-lapachone at an acidic pH (e.g. a physiologically acidic pH). In some embodiments, the therapeutic agent is a β-lapachone prodrug with a linkage of: ketal, acyl hydrazone, aliphatic imine, aromatic imine bond, or a combination thereof. In some embodiments, the ketal, acyl hydrazone, aliphatic imine, or aromatic imine bond is a pH sensitive linkage. In some embodiments, the prodrug is selected from:

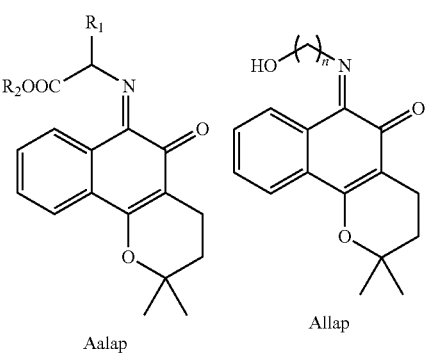

Aalap

Allap

-continued

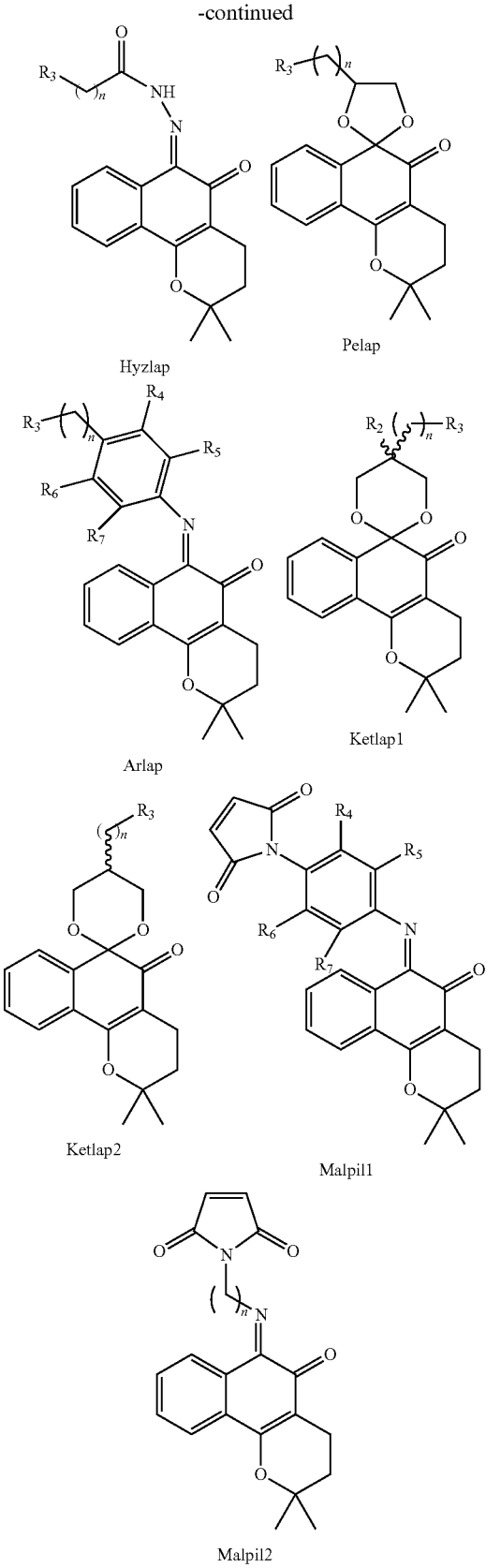

wherein $R_1$ is a side chain of D or L amino acids; $R_2$ is an alkyl group or an aromatic group; $R_3$ is $NH_2$, OH, or SH;

each of $R_4$, $R_5$, $R_6$, and $R_7$ is independently H, X, $OCH_3$, or $CH_3$; X is a halogen; and n is an integer between 1 and 20. In some embodiments, X is Cl, Br, I; or F. In some embodiments, $R_2$ is $CH_3$, $CH_2CH_3$, or Bzl. Non-limiting examples of prodrugs of the invention include the following:

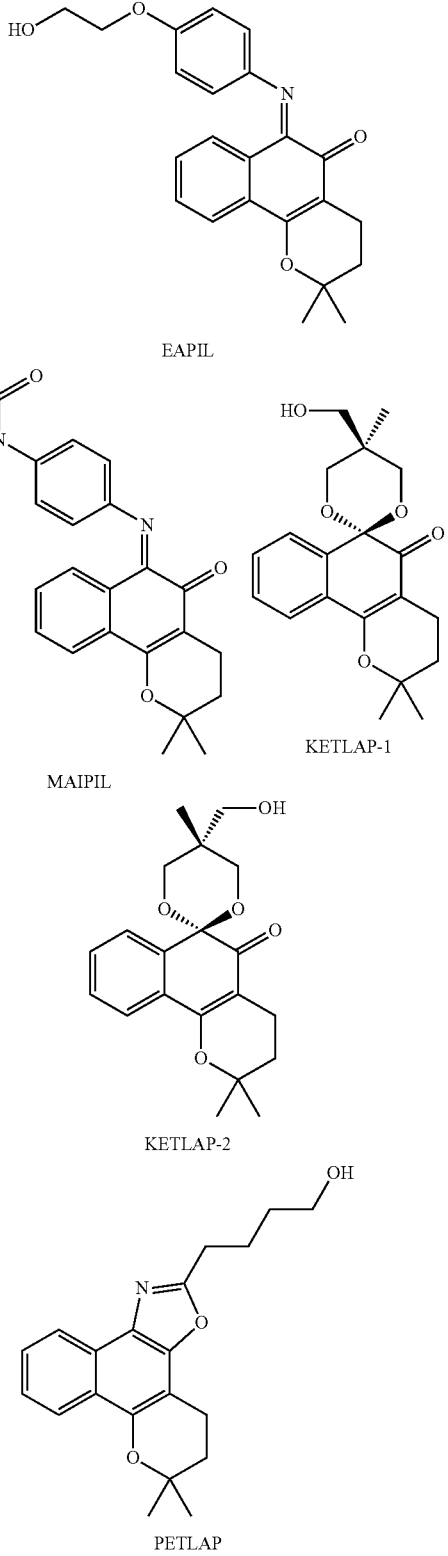

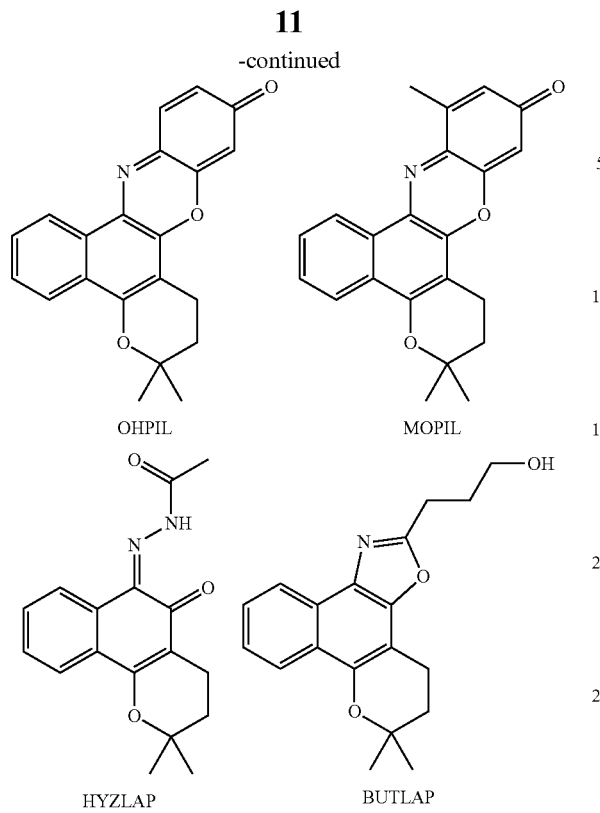

OHPIL  MOPIL

HYZLAP  BUTLAP

In some embodiments, the prodrug is Eapil or Malpil. In some embodiments, the prodrug (e.g. Eapil and Malpil) demonstrates optimal pH sensitivity in pH 5.0-7.4 range. In some embodiments, the therapeutic agent is a β-lapachone prodrug with an aromatic imine bond. In some embodiments, the aromatic imine bond is a pH sensitive linker. In some embodiments, the aromatic imine bond is sensitive to pHs between about 5.0 and about 7.4. In some embodiments, the biocompatible polymeric prodrug micelle comprises a block copolymer. In some embodiments, the block copolymer comprises pH responsive segments (e.g. to increase pH sensitivity of the micelle). In some embodiments, the block copolymer comprises biocompatible hydrophilic segment of different lengths of PEG. In some embodiments, the block copolymers and prodrugs are linked by any suitable conjugation method, for example, a bond selected from: an ester bond, amide bond, disulfide bond, acyl hydrazone bond, ketal bond. In some embodiments, the block copolymer comprises poly(L-cysteine) blocks or other polypeptide-based polymers. In some embodiments, the block copolymer is: PEG-PDPA-PDMS. In some embodiments, the biocompatible polymeric prodrug micelle has the formula:

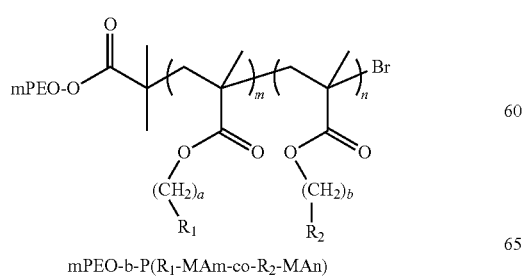

mPEO-b-P(R$_1$-MAm-co-R$_2$-MAn)

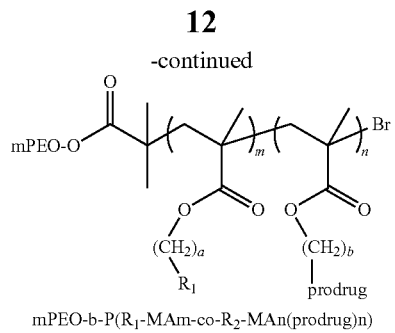

mPEO-b-P(R$_1$-MAm-co-R$_2$-MAn(prodrug)n)

wherein R1 and R2 are each independently selected from:

| Code(R1 and R$_2$) | Structure |
| --- | --- |
| PDMA | 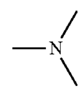 |
| PDEA | 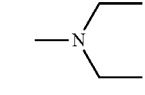 |
| PDiPA | 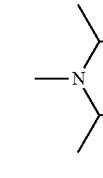 |
| PDnPA | 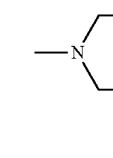 |
| PDBA | 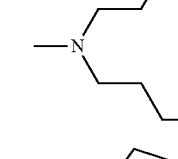 |
| Pc5A | 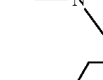 |
| Pc6A | 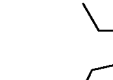 |
| Pc7A | 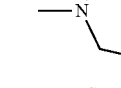 |
| PDMS | 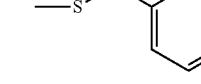 |
| PDBS | 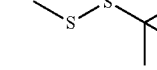 |

-continued

| Code(R1 and R₂) | Structure |
|---|---|
| PDPS | —S—S—C₆H₅ |

In some embodiments, the block copolymer is: PEG-PCys.

In some embodiments, the loading density of β-lapachone compositions disclosed herein are over 10 wt %., 20 wt %., or 30 wt %. In some embodiments, the β-lapachone prodrug micelles are stable at pH 7.4, but can dramatically increase drug release at acidic pH (e.g. pH=5.0 or 6.0).

BRIEF DESCRIPTION OF THE DRAWINGS

FIG. 1a shows HPLC detection of prodrug (6) conversion at 5, 90, and 600 mins at pH 5.0. FIG. 1b shows quantitative analysis of prodrug (6) conversion at pH 5.0, showing both the decrease of prodrug (6) and formation of β-lap. FIG. 1c shows a comparison of β-lap formation from prodrug (6) at pH 5.0, 6.5 and 7.4.

FIGS. 3a and 3b show A549 cells treated with free β-Lap for 2 hours and 24 hours, respectively. FIGS. 3c, 3d, 3e and 3f show cells treated with prodrug (6)-conjugated micelles for 2 hours, 8 hours, 12 hours and 24 hours, respectively. DIC is a specific NQO1 inhibitor and used to block fβ-Lap induced cytotoxicity.

DETAILED DESCRIPTION OF THE INVENTION

Figure 1:
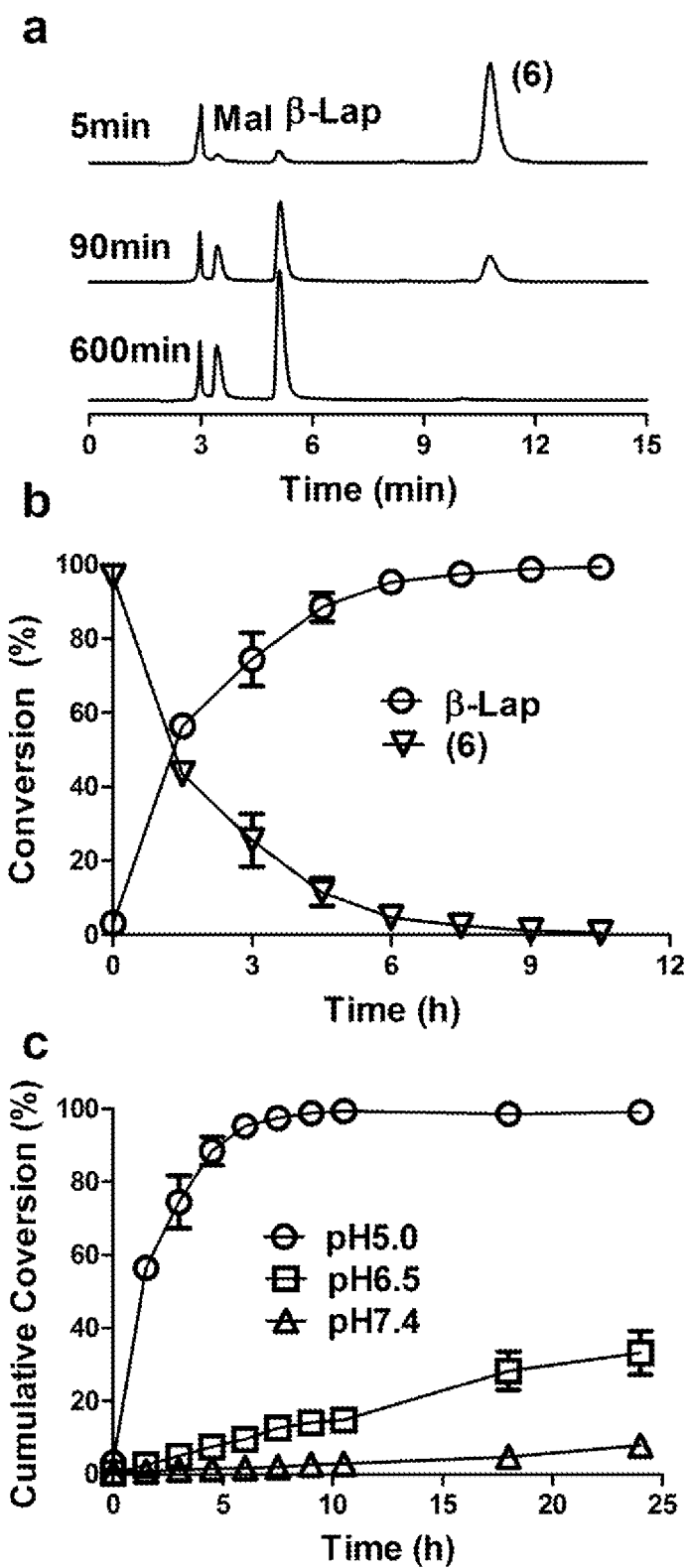
FIG. 1 shows conversion of prodrug (6) into β-Lap at different pH.

Disclosed herein are compositions comprising a polymer conjugated to a pH-sensitive prodrug of beta-lapachone, and micelle compositions of such polymer-prodrug conjugates. The pH-sensitive prodrug comprises a pH-sensitive linker. In some embodiments, the pH-sensitive linker has a pH sensitivity such that the drug is not released (or is released much more slowly) from the prodrug at normal physiological pH (7.4), but releases beta-lapachone at a lower pH (or is released much more rapidly at the lower pH), such as in the more acidic environment of a tumor, early endosomes, late endosomes, or lysosomes. Thus, the micelles may improve drug specificity and bioavailability in cancer cells. Further, the micelle formulations may result in one or more of the following: improved drug solubility, drug yield, shelf life, plasma stability and plasma circulation time, improved loading density of beta-lap, improved safety with no hemolysis, enhanced drug delivery into tumor cells, improved drug tissue distribution at tumor tissue, and enhanced cytotoxicity. Furthermore, disclosed herein are compositions comprising pH-sensitive micelles, thus allowing for dual pH sensitivity of beta-lap release, and potential for further improvements in drug specificity and delivery, and enhanced cytotoxicity.

DEFINITIONS

As used herein, "alkyl" indicates any saturated hydrocarbon moiety, including, for example, straight chain, branched chain, or cyclic (including fused and spiro bicyclic and polycyclic) saturated hydrocarbon moieties which may optionally be substituted with one or more additional saturated hydrocarbon moieties.

As used herein, "pH-sensitive micelle", "pH-activatable micelle" and "pH-activatable micellar (pHAM) nanoparticle" are used interchangeably herein to indicate a micelle comprising one or more block copolymers, which disassociates depending on the pH (e.g. below a certain pH). As a non-limiting example, at a certain pH, the block copolymer is substantially in micellar form. As the pH changes (e.g. decreases), the micelles begin to disassociate, and as the pH further changes (e.g. further decreases), the block copolymer is present substantially in disassociated (non-micellar) form.

As used herein, "pH transition range" indicates the pH range over which the pH-sensitive micelles disassociate. In some embodiments, the pH transition range is the pH response sharpness. Dynamic light scattering (DLS), transmission electron microscopy (TEM), or an external fluorophore (e.g. pyrene) can be used to characterize the pH-dependent micellization behaviors.

As used herein, "pH transition value" ($pH_t$) indicates the pH at which half of the micelles are disassociated. Dynamic light scattering (DLS) or an external fluorophore (e.g. pyrene) can be used to characterize the pH-dependent micellization behaviors.

As used herein, the term "treating" refers to a clinical intervention designed to alter the natural course of clinical pathology of the disease or disorder being treated (e.g., cancer). Desirable effects of treatment include, for example, ameliorating or palliating the disease state, slowing or reversing the progression of the disorder, remission, or improved prognosis.

As used herein, the term "effective amount" refers to an amount effective, at dosages and for periods of time necessary, to achieve the desired therapeutic or prophylactic result. An effective amount can be provided in one or more administrations.

As used herein, "individual" indicates an animal, preferably a mammal, including humans, primates, laboratory animals (e.g. rats, mice, etc.), farm animals (e.g. cows, sheep, goats, pigs, etc.), pets (e.g. dogs, cats, etc.), and sport animals (e.g. horses, etc.). In some embodiments, an individual is a human.

As used herein "PEG" and "PEO" are used interchangeably to refer to a polymer of ethylene oxide.

Reference to "about" a value or parameter herein also includes (and describes) embodiments that are directed to that value or parameter per se.

As used herein and in the appended claims, the singular forms "a," "an," and "the" include plural reference unless the context clearly indicates otherwise.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions.

It is to be understood that any of the compositions described herein may be used in any of the methods as described herein, unless context clearly indicates otherwise.

pH Sensitive Prodrugs of Beta-Lapachone

In one aspect of the invention, the pH sensitive prodrugs of beta-lapachone comprise a pH-sensitive linker selected from the group consisting of: an aryl imine and an aliphatic imine. The aryl and aliphatic imine linkers have the general structure:

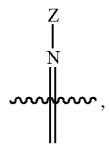

wherein Z is an aryl or aliphatic group. The aryl or aliphatic imine linkers may be formed on either of beta-lapachone's two oxo groups $O_1$ or $O_2$:

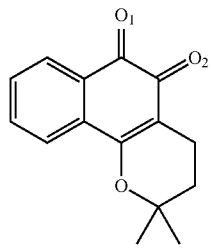

In some embodiments, the linker is formed on $O_1$, for example:

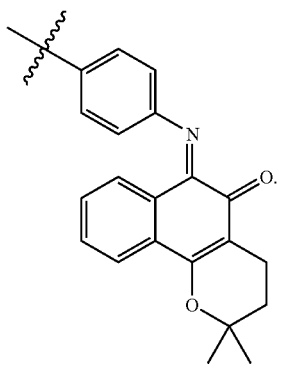 [SMILES: *c1ccc(/N=C2/C(=O)C3=C(OC(C)(C)CC3)c3ccccc32)cc1]

In some embodiments the linker does not cyclize with the other oxo group (examples of cyclized prodrugs include Petlap in Example 1, and Ohpil and Mopil in Example 3).

In general, the pH-sensitive linkers are sensitive to a pH that is useful in a physiological setting. For example, extracellular tumor environments have a lower pH (6.3-6.7) than normal tissues (7.4). Additionally, early endosomes (e.g. 5.9-6.2), late endosomes/lysosomes (e.g. 5.0-5.5) have a lower pH than normal tissues. Exposure of a linker having a pH-sensitivity at a lower pH (e.g. 6.0) to the tumor extracellular environment results in preferential release of the beta-lapachone at the tumor site rather than to normal tissues. In some embodiments, the linker is sensitive to pH between about 5.0 and about 7.4. In some embodiments, the linker is sensitive to pH between about 5.0 and about 7.0. In some embodiments, the linker is sensitive to pH between about 5.0 and 6.5. In some embodiments, the linker is sensitive to pH between about 5.0 and 5.5. In some embodiments, the linker is sensitive to pH between about 5.9 and 6.2. In some embodiments, the linker is sensitive to pH between about 5.5 and 6.5.

In some embodiments, the pH-sensitive linker is an aryl imine. In general, the aryl group has about 5 to about 14 ring atoms. In some embodiments, the aryl group has 5-7 ring atoms. The aryl group ring atoms may be all carbon, or may comprise one or more heteroatoms, such as S, O, and/or N. In some embodiments, aryl group is a phenyl group. The aryl group may optionally comprise one or more (e.g. 2, 3, 4, 5, or more) substituents, provided that the substituents do not result in a prodrug that lacks a pH-sensitive linker. When more than one substituent is present, the substituents may be the same or different. In some embodiments, the aryl group comprises one substituent. The substituents may be present in the ortho, meta, or para positions. In a preferred embodiment, a substituent is present in the para position. In some embodiments, the aryl group comprises one substituent at the para position.

In some embodiments, the pH-sensitive linker is an aliphatic imine. In some embodiments, the aliphatic group is a straight chain or branched alkyl group. The aliphatic group may optionally comprise one or more (e.g. 2, 3, 4, 5, or more) substituents, provided that the substituents do not result in a prodrug that lacks a pH-sensitive linker. In preferred embodiments, the Ca of the aliphatic imine (i.e. the carbon directly linked to the nitrogen of the imine) comprises at least one substituent. In some embodiments, the Ca of the aliphatic imine comprises two substituents. In some embodiments, the Ca of the aliphatic imine comprises two substitutents which are both methyl, for example:

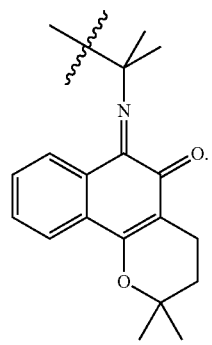 [SMILES: *C(C)(C)N=C1C(=O)C2=C(OC(C)(C)CC2)c2ccccc21]

The substituents on the aryl or aliphatic groups may comprise functional groups which are capable of linking the prodrug to the polymer. For example, a substituent may comprise a moiety selected from the group consisting of: —OH, —NH$_2$, —SH, or

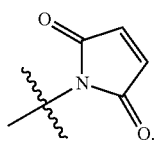 [SMILES: *N1C(=O)C=CC1=O]

In some embodiments, the moiety is

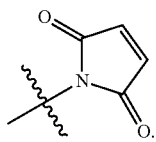

In some embodiments, the linkage between the prodrug and the polymer is selected from the group consisting of an amide bond, an ester bond, a thioether bond, and a disulfide bond.

Exemplary pH-sensitive beta-lapachone prodrugs include the following:

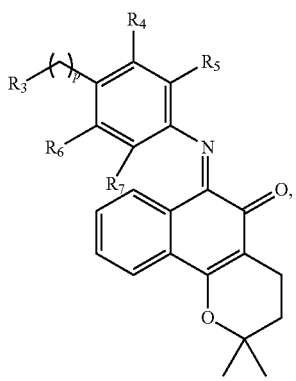

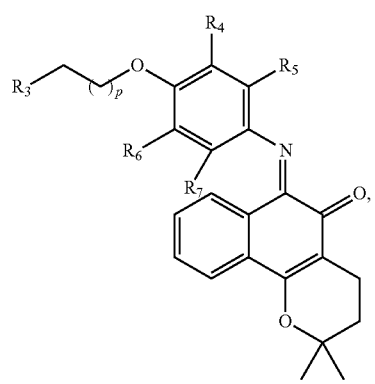

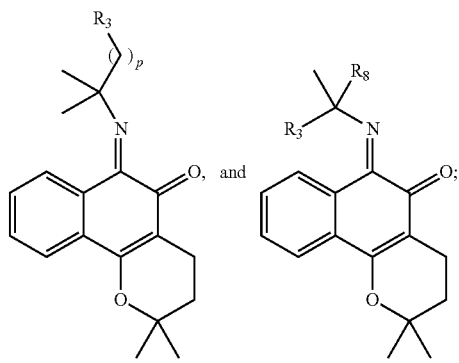

wherein R$_8$ is a side chain of a D or L amino acid other than —H; R$_3$ is —NH$_2$, —OH, —SH, or

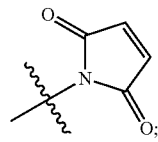

each of R$_4$, R$_5$, R$_6$, and R$_7$ is independently —H, —X, —OCH$_3$, or —CH$_3$; X is a halogen; and p is an integer between 0 and 20. In some embodiments, R$_8$ is —CH$_3$. In some embodiments, R$_3$ is

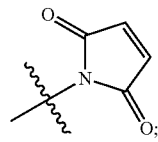

In some embodiments, R$_3$ is —OH. In some embodiments, each of R$_4$, R$_5$, R$_6$, and R$_7$ is H. In some embodiments, X is Cl, Br, I, or F. In some embodiments, p is 0-6. In some embodiments, p is 0-4. In some embodiments, p is 0-2. In various embodiments, p is 0, 1, 2, 3, 4, 5, 6, 7, 8, 9, 10, 11, or 12. In some embodiments, the prodrug is

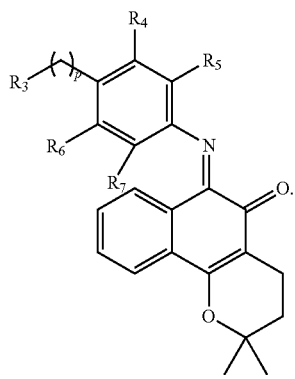

In some embodiments, the prodrug is

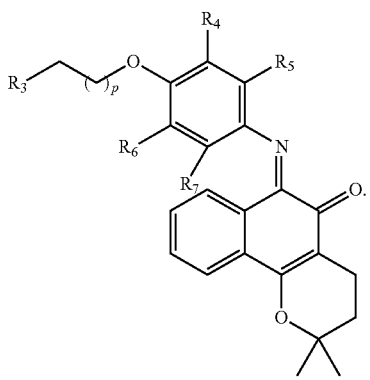

In some embodiments, the prodrug is

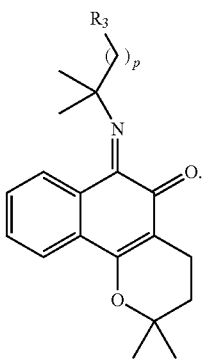

Non-limiting examples of prodrugs of the invention include:

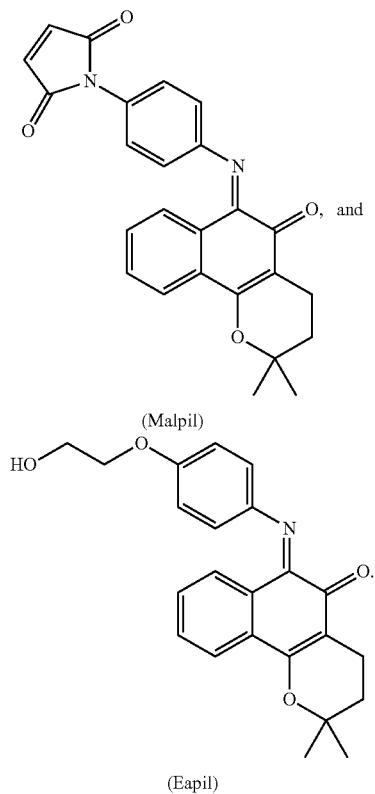

Exemplary methods of making the prodrugs from beta-lapachone are described in the Examples below.

The prodrugs comprise a suitable functional group for enabling conjugation of the prodrug to the polymer. Non-limiting examples of such functional groups include, for example, —OH, —NH$_2$, —SH, and

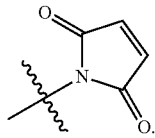

The linkage between the prodrug and the polymer may or may not be pH sensitive. In some embodiments, the linkage between the prodrug and the polymer is not pH sensitive. Conjugation of the prodrug to the polymer may be accomplished by one skilled in the art. For example, a polymer containing one of the following functional groups:

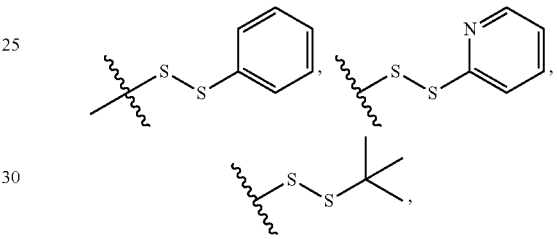

or —SH may yield the following thioether linkage:

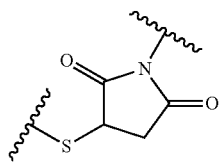 [SMILES: *SC1CC(=O)N(*)C1=O]

by utilizing a maleimide group present on the prodrug.

Micelles

In another aspect of the invention are compounds comprising a beta-lapachone prodrug of the invention conjugated to a polymer, wherein the polymer-prodrug compound is capable of forming a micelle. The invention further provides micelle compositions comprising such polymer-prodrug compounds. The micelle compositions are useful in treating a tumor, for example, as the extracellular tumor environment has a lower pH (6.3-6.7) than physiological pH 7.4, and thus the beta-lapachone is preferentially released at the tumor site via the pH-sensitive linker. Micelles may also be delivered to tumor endosomes and/or lysosomes, thus preferentially releasing beta-lap at the tumor site via the pH-sensitive linker.

In some embodiments, the polymer comprises a block copolymer comprising a hydrophilic polymer segment (e.g. polyethylene oxide (PEO)) and a hydrophobic polymer segment. Examples of hydrophilic and hydrophobic polymer segments are described in more detail below. One or more block copolymers (e.g. 2, 3, 4, 5, or more) may be used to form a micelle. In some embodiments, a composition comprises a single type of micelle. In some embodiments, two or more (e.g. 2, 3, 4, 5, or more) different types of micelles may be combined to form a mixed-micelle composition.

One or more prodrug molecules (e.g. 2, 3, 4, 5, 6, 7, 8, 8, 10, 10-20, 20-30, 30-40, 40-50, or more than 50) may be conjugated to each polymer. In some embodiments, the prodrug is conjugated to the hydrophobic polymer segment. In general, upon micelle formation, the prodrug is encapsulated within the micelle. In various embodiments, the loading density of beta-lapachone prodrugs are over 10 wt %, over 20 wt %, or over 30 wt %.

In some embodiments, the micelle further comprises a labeling moiety and/or a targeting moiety (e.g. moiety targeting a cancer cell surface receptor). For example, a targeting moiety can target a cancer cell surface marker, such as an angiogenesis biomarker. A targeting moiety may enable a micelle to be taken up into endosomes and lysosomes of cancer cells by receptor-mediated endocytosis. In some embodiments, the targeting moiety binds to an angiogenesis biomarker. In some embodiments, the angiogenesis biomarker is VEGF-VEGFR complex or endoglin. In some embodiments, the targeting moiety binds to VEGFR2. In some embodiments, the targeting moiety is a Fab' fragment of RAFL-1 mAb. In some embodiments, the targeting moiety binds to $\alpha_v\beta_3$ integrin. In some embodiments, the targeting moiety is cRGDfK.

In some embodiments, the micelle is a pH-sensitive micelle, in which micelle formation/disassociation is driven by pH. For example, at a higher pH, the polymer-prodrug forms a stable micelle, but at a lower pH, the micelle disassociates. This may further improve the targeting of beta-lapachone to the tumor site, as the micelle itself does not dissociate at physiological pH but may disassociate at the lower pH of the tumor (thus increasing exposure of the prodrug to the surrounding milieu). In some embodiments, the polymer comprises a pH responsive segment which may drive micelle formation and dissociation. For example, a pH-responsive segment may comprise an amine group which protonates at lower pH. Protonation of the amine group increases the pH responsive segment's hydrophilicity, thus resulting in micelle dissociation. At higher pH, the amine is not protonated, thus increasing the segment's hydrophobicity and driving micelle formation. In some embodiments, the hydrophobic polymer segment is the pH responsive segment. Specific examples of pH-responsive segments and pH-responsive micelles are described in more detail below.

Without wishing to be bound by theory, the use of micelles in cancer therapy may enhance anti-tumor efficacy and reduce toxicity to healthy tissues, in part due to the size of the micelles. While small molecules such as certain chemotherapeutic agents (e.g. beta-lapachone) can enter both normal and tumor tissues, micelle nanoparticles may preferentially cross leaky tumor vasculature. In some embodiments, the micelles have a size of about 10 to about 200 nm. In some embodiments, the micelles have a size of about 20 to about 100 nm. In some embodiments, the micelles have a size of about 30 to about 50 nm.

Examples of methods of generating micelles from block copolymers may be found in the Examples below. For example, block copolymer is first dissolved in organic solvent (e.g. THF) and may be added to an aqueous solution, optionally under sonication, wherein the copolymer self-assemble to form micelles in the solution.

Poly(Cys) Micelles

In some embodiments, the hydrophobic polymer segment comprises a poly(L-cysteine) block. Poly(L-cysteine) blocks biodegrade over time, thus exposing the prodrug to the surrounding milieu. The poly(L-cysteine) block generally comprises about 5 to about 50 cysteine residues, and in various embodiments may comprise about 20 to about 50 cysteine residues or about 30 to about 40 cysteine residues. In some embodiments, the prodrug is conjugated to the poly(Cys) block by a thioether linkage. The prodrug may be conjugated to one or more cysteines residues in the polymer, and in some embodiments, is conjugated to at least about 10%, at least about 20%, at least about 30%, at least about 40%, at least about 50%, at least about 60%, at least about 70%, at least about 80%, at least about 90%, or all or substantially all of the cysteine residues. In some embodiments, the prodrug is Malpil. In some embodiments, the prodrug is Eapil.

In some embodiments, the poly(Cys) block is conjugated to a hydrophilic segment comprising polyethylene oxide (PEO). In some embodiments, the PEO is about 2 kD to about 20 kD in size. In some embodiments, the PEO is about 2 kD to about 10 kD in size. In some embodiments, the PEO is about 4 kD to about 6 kD in size. In some embodiments, the PEO is about 5 kD in size.

Exemplary methods of making the poly(L-Cys) polymers of the invention, and conjugating them to beta-lapachone prodrugs are described in the Examples below, for example, in Example 7 below.

Exemplary pH-Sensitive Micelles

The pH-sensitive micelles may comprise a block copolymer comprising a hydrophilic polymer segment and a hydrophobic polymer segment, wherein the hydrophobic polymer segment comprises an ionizable amine group to render pH sensitivity. The block copolymers form pH-sensitive micelles based on the supramolecular self-assembly of these ionizable block copolymers. For example, at higher pH, the block copolymers assemble into micelles, whereas at lower pH, ionization of the amine group in the hydrophobic polymer segment results in dissociation of the micelle. Without wishing to be bound by theory, micelle formation and its thermodynamic stability are driven by the delicate balance between the hydrophobic and hydrophilic segments. The ionizable groups may act as tunable hydrophilic/hydrophobic blocks at different pH values, which may directly affect the dynamic self-assembly of micelles. Without wishing to be bound by theory, micellization may sharpen the ionization transition of the amines in the hydrophobic polymer segment, rendering fast and ultra-sensitive pH response. Different block copolymers may be selected to provide micelles having different transition pH values within physiological range, in order to achieve selective activation within various environments, such as tumors (e.g. the extracellular environment of tumors, early endosomes, late endosomes/lysosomes).

Specific pH conditions (e.g. acidic pH present in tumors, early endosomes, late endosomes/lysosomes) may lead to rapid protonation and dissociation of micelles into unimers, thereby exposing the prodrug. In some embodiments, the micelle provides stable prodrug encapsulation at physiological pH (pH 7.4), but can quickly expose the prodrug in acidic environments. The micelles may provide one or more advantages in therapeutic applications, such as: (1) disassociation of the micelle (and rapid exposure of prodrug) within a short amount of time (e.g. within minutes) under certain pH environments (e.g. acidic environments), as opposed to hours or days for previous micelle compositions; (2) increased selective targeting of drug delivery to the desired site (e.g. tumor), which may enhance drug efficacy and reduce toxicity to healthy cells; (3) prolonged blood circulation times; and (4) responsiveness within specific narrow pH ranges.

In some embodiments, the block copolymer comprises a hydrophilic polymer segment and a hydrophobic polymer segment, wherein the hydrophilic polymer segment comprises a polymer selected from the group consisting of: poly(ethylene oxide) (PEO), poly(methacrylate phosphatidyl choline) (MPC), and polyvinylpyrrolidone (PVP), wherein the hydrophobic polymer segment comprises

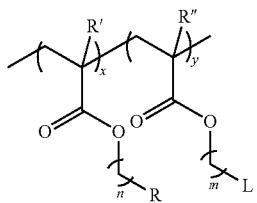

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, wherein x is about 10 to about 50 in total, wherein L is the prodrug conjugated to the polymer by a linker moiety, wherein y is 1 to about 30, wherein R" is —H or —CH$_3$; wherein m is 1 to about 10; and wherein the moieties comprising R and the moieties comprising L may be arranged in any order. For example, x may be about 10 to about 50 as a continuous segment (i.e. a continuous segment of about 10 to about 50 monomer units), or other moieties (e.g. moieties comprising the prodrug) may be interspersed between the monomer units, for example as described in more detail below.

Block copolymers of the invention include, for example, compounds of Formula I:

(Formula I)

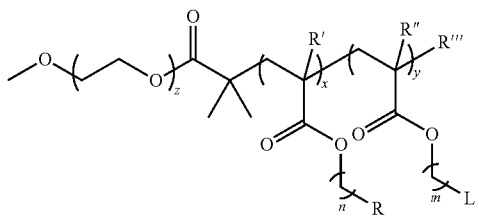

wherein z is such that the PEO is about 2 kD to about 20 kD in size, wherein x, y, n, m, R, L, R' and R" are as defined above, wherein R'" is any suitable moiety, and wherein the following portion of the structure:

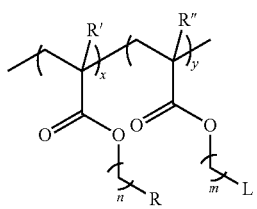

may be arranged in any order.

In some embodiments, R'" is an end group resulting from a polymerization reaction. For example, R'" may be —Br when atom transfer radical polymerization (ATRP) is used. For example, R'" may be a sulfur-containing group such as thiolate or a thioester when reversible addition-fragmentation chain transfer (RAFT) is used. In some embodiments, R'" is —Br. In some embodiments, R'" is thiolate. In some embodiments, R'" is a thioester. The end group may optionally be further modified following polymerization with an appropriate moiety.

In some embodiments, the following portion of the structure:

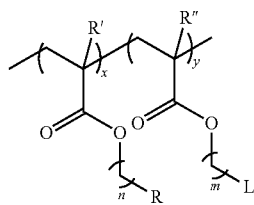

is randomized, i.e.:

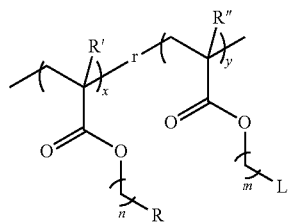

wherein r (or co) indicates a random ordering of the R containing moieties and the L containing moieties (i.e. the R containing moieties and the L containing moieties are randomly interspersed).

In some embodiments, the following portion of the structure:

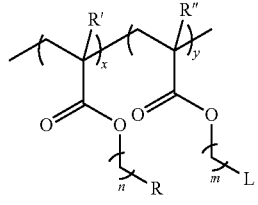

is arranged sequentially. For example, the R containing moieties may be present as a single block, with the L containing moieties present as a single block either preceding or following the R containing moieties. Other arrangements may also be utilized.

In some embodiments, the hydrophilic polymer segment comprises poly(ethylene oxide) (PEO). In some embodiments, the hydrophilic polymer segment comprises poly (methacrylate phosphatidyl choline) (MPC). In some embodiments, the hydrophilic polymer segment comprises polyvinylpyrrolidone (PVP). In general, the PEO, MPC, or PVP polymer in the hydrophilic polymer segment is about 2 kD to about 20 kD in size. In some embodiments, the polymer is about 2 kD to about -10 kD in size. In some embodiments, the polymer is about 2 kD to about 5 kD in size. In some embodiments, the polymer is about 3 kD to about 8 kD in size. In some embodiments, the polymer is about 4 kD to about 6 kD in size. In some embodiments, the polymer is about 5 kD in size. In some embodiments, the polymer has about 100 to about 130 monomer units. In some embodiments, the polymer has about 110 to about 120 monomer units. In some embodiments, the polymer has about 114 monomer units. In some embodiments, the polydispersity index (PDI) of the polymer is less than about 1.2. In some embodiments, the polydispersity index (PDI) of the polymer is less than about 1.1.

Suitable PEO, MPC, and PVP polymers may be purchased (for example, PEO polymers may be purchased from Aldrich Sigma) or may be synthesized according to methods known in the art. In some embodiments, the hydrophilic polymer can be used as an initiator for polymerization of the hydrophobic monomers to form a block copolymer.

For example, MPC polymers (e.g. narrowly distributed MPC polymers) can be prepared by atom transfer radical polymerization (ATRP) with commercially available small molecule initiators such as ethyl 2-bromo-2-methylpropanoate (Sigma Aldrich). These resulting MPC polymers can be used as macromolecular ATRP initiators to further copolymerize with other monomers to form block polymers such as MPC-b-PDPA. PEO-b-PR block copolymers can be synthesized using atom transfer radical polymerization (ATRP) or reversible addition-fragmentation chain transfer (RAFT) methods (See e.g. Australian Journal of Chemistry Volume: 58 Issue: 6 Pages: 379-410 (2005); Progress in Polymer Science Volume: 32 Issue: 1 Pages: 93-146 (2007). ATRP or RAFT allows for living polymerization which can yield PEO-b-PR copolymers with narrow polydispersity (<1.1). Different metharylate or acrylate monomers can be used to produce PR segments with different pH sensitivity.

The hydrophobic polymer segment may comprise:

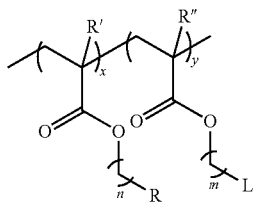

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, wherein x is about 10 to about 50 in total, wherein L is the prodrug conjugated to the polymer by a linker moiety, wherein y is 1 to about 30, wherein R" is —H or —CH$_3$; wherein m is 1 to about 10; and wherein the moieties comprising R and the moieties comprising L may be arranged in any order.

In some embodiments, n is 1 to 4. In some embodiments, n is 2. In various embodiments, n is 1, 2, 3, 4, 5, 6, 7, 8, 9, or 10.

In some embodiments, R' is —CH$_3$. In some embodiments, R' is —H.

In some embodiments, x is about 10 to about 30 in total. In some embodiments, x is about 10 to about 20 in total. In some embodiments, wherein x is about 15 in total.

In some embodiments, R$^1$ and R$^2$ together have from 5 to 14 carbons. In some embodiments, R$^1$ and R$^2$ together have from 5 to 12 carbons. In some embodiments, R$^1$ and R$^2$ together have from 5 to 10 carbons. In some embodiments, R$^1$ and R$^2$ together have from 5 to 8 carbons. In some embodiments, R$^1$ and R$^2$ together have from 6 to 12 carbons. In some embodiments, R$^1$ and R$^2$ together have from 6 to 10 carbons. In some embodiments, R$^1$ and R$^2$ together have from 6 to 8 carbons. In various embodiments, R$^1$ and R$^2$ together have 5, 6, 7, 8, 9, 10, 11, 12, 13, 14, 15, or 16 carbons. In some embodiments, R$^1$ and R$^2$ each have 3 to 8 carbons. In some embodiments, R$^1$ and/or R$^2$ comprise 3 carbons. In some embodiments, R$^1$ and/or R$^2$ comprise 4 carbons. In some embodiments, R$^1$ and/or R$^2$ comprise 5 carbons. In some embodiments, R$^1$ and/or R$^2$ comprise 6 carbons. In some embodiments, R$^1$ and/or R$^2$ comprise 7 carbons. In some embodiments, R$^1$ and/or R$^2$ comprise 8 carbons. In some embodiments, R$^1$ and R$^2$ are the same. In some embodiments, R$^1$ and R$^2$ are different. In some embodiments, R$^1$ and R$^2$ are each independently straight or branched alkyl. In some embodiments, R$^1$ and R$^2$ are each straight alkyl. In some embodiments, R$^1$ and R$^2$ are each branched alkyl. Suitable alkyl groups for R$^1$ and R$^2$ include, for example, methyl, ethyl, propyl, butyl, pentyl, hexyl, heptyl, octyl, nonyl, decyl, undecyl, dodecyl, tridecyl, tetradecyl, and pentadecyl, including various possible skeletal isomers for each alkyl group such as n-, iso-, sec-, tert-, neo-, etc., provided the total number of carbons in R is from 5 to 16. In some embodiments, R$^1$ and R$^2$ are propyl. In some embodiments, propyl is iso-propyl. In some embodiments, propyl is n-propyl. In some embodiments, R$^1$ and R$^2$ are butyl. In some embodiments, butyl is n-butyl. In some embodiments, butyl is iso-butyl. In some embodiments, butyl is sec-butyl. In some embodiments, butyl is t-butyl. In some embodiments, R$^1$ and R$^2$ join to form a ring. The ring may optionally be substituted with one or more alkyl groups, provided the total number of carbons in R is from 5 to 16. In some embodiments, R$^1$ and R$^2$ together form a ring having 5 to 10 carbons. In some embodiments, R$^1$ and R$^2$ together form a ring having 5 to 8 carbons. In some embodiments, R$^1$ and R$^2$ together form a ring having 5 to 7 carbons. In some embodiments, R$^1$ and R$^2$ together are —(CH$_2$)$_5$—. In some embodiments, R$^1$ and R$^2$ together are —(CH$_2$)$_6$—.

In some embodiments, R" is —CH$_3$. In some embodiments, R" is —H.

In some embodiments, m is 1 to 4. In some embodiments, m is 2. In various embodiments, m is 1, 2, 3, 4, 5, 6, 7, 8, 9, or 10.

In some embodiments, y is about 3 to about 10. In some embodiments, y is about 10 to about 30. In some embodiments, y is about 3. in various embodiments, y is about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In some embodiments, the linker in L is selected from the group consisting of an ester, an amide, a thioether, and a disulfide. In some embodiments, the linker in L is a thioether.

The prodrug in L may be any of the prodrugs described herein. In some embodiments, the prodrug is:

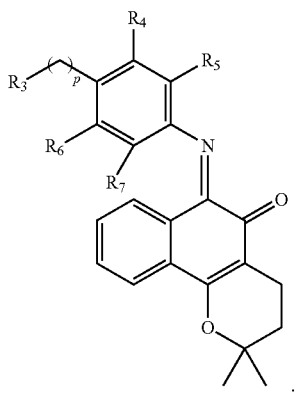

In some embodiments, the prodrug is:

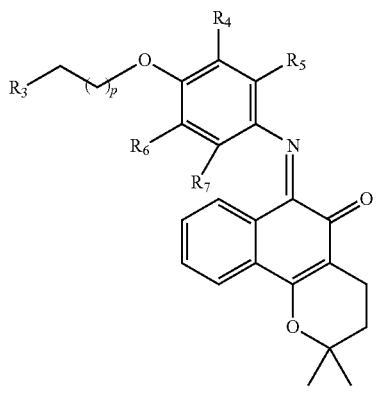

In some embodiments, the prodrug is:

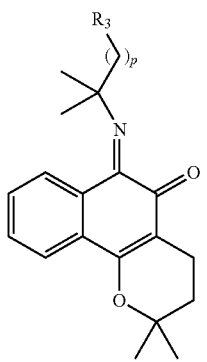

In some embodiments, the prodrug is:

In some embodiments, the prodrug is Mapil. In some embodiments, the prodrug is Eapil.

The hydrophobic polymer segment may be synthesized according to, e.g. Atom Transfer Radical Polymerization (ATRP) or reversible addition-fragmentation chain transfer (RAFT). In some embodiments, the polydispersity index (PDI) for the hydrophobic polymer segment is less than about 1.2. In some embodiments, the polydispersity index (PDI) for the hydrophobic polymer segment is less than about 1.1.

Non-limiting examples of block copolymers of Formula I are provided in Table A.

TABLE A

Exemplary block copolymers

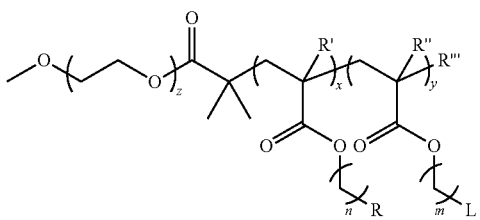

| Compound | R' | R¹/R² | n | z | R'' | m | x | y | L | R''' |
|---|---|---|---|---|---|---|---|---|---|---|
| mPEG-b-P(DPA$_{15}$-co-PDMS(6)$_3$) | —CH$_3$ | iPr/iPr | 2 | 114 | —CH$_3$ | 2 | 15 | 3 | —S-Malpil | Br |
| mPEG-b-P(DBA$_{15}$-co-PDMS(6)$_3$) | —CH$_3$ | nBu/nBu | 2 | 114 | —CH$_3$ | 2 | 15 | 3 | —S-Malpil | Br |
| m-PEG-b-P(C6A$_{15}$-co-PDMS(6)$_3$) | —CH$_3$ | —(CH$_2$)$_5$— | 2 | 114 | —CH$_3$ | 2 | 15 | 3 | —S-Malpil | Br |
| mPEG-b-P(C7A$_{15}$-co-PDMS(6)$_3$) | —CH$_3$ | —(CH$_2$)$_6$— | 2 | 114 | —CH$_3$ | 2 | 15 | 3 | —S-Malpil | Br |
| mPEG-b-P(DPA$_{15}$-co-(Eapil)$_3$) | —CH$_3$ | iPr/iPr | 2 | 114 | —CH$_3$ | 2 | 15 | 3 | —COO-Eapil | Br |
| mPEG-b-P(DBA$_{15}$-co-(Eapil)$_3$) | —CH$_3$ | nBu/nBu | 2 | 114 | —CH$_3$ | 2 | 15 | 3 | —COO-Eapil | Br |
| mPEG-b-P(C6A$_{15}$-co-(Eapil)$_3$) | —CH$_3$ | —(CH$_2$)$_5$— | 2 | 114 | —CH$_3$ | 2 | 15 | 3 | —COO-Eapil | Br |
| mPEG-b-P(C7A$_{15}$-co-(Eapil)$_3$) | —CH$_3$ | —(CH$_2$)$_6$— | 2 | 114 | —CH$_3$ | 2 | 15 | 3 | —COO-Eapil | Br |

In Table A, the following portion of the structure:

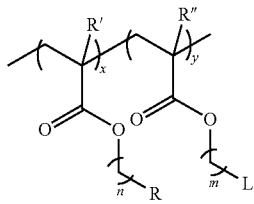

is randomized, i.e.:

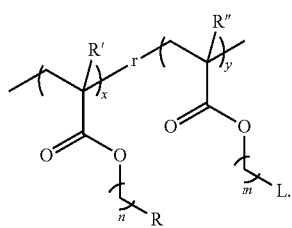

With regards to the compounds described herein, it is to be understood that polymerization reactions may result in a certain variability of polymer length, and that the numbers described herein indicating the number of monomer units within a particular polymer (e.g. x, y, z) may indicate an average number of monomer units. In some embodiments, a polymer segment described herein (e.g. the hydrophobic polymer segment, the hydrophilic polymer segment) has a polydispersity index (PDI) less than about 1.2. In some embodiments, the polydispersity index (PDI) for the polymer segment is less than about 1.1. In some embodiments, the polydispersity index (PDI) for the block copolymer is less than about 1.2. In some embodiments, the polydispersity index (PDI) for the block copolymer is less than about 1.1.

The pH-sensitive micelle compositions may advantageously have a narrow pH transition range, in contrast to other pH sensitive micelle compositions in which the pH response is very broad (i.e. 2 pH units). In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the micelles have a pH transition range of less than about 0.25 pH unit.

The micelles may have different pH transition values within physiological range, in order to target specific microenvironments. In some embodiments, the micelles have a pH transition value of about 5 to about 8. In some embodiments, the micelles have a pH transition value of about 5 to about 6. In some embodiments, the micelles have a pH transition value of about 6 to about 7. In some embodiments, the micelles have a pH transition value of about 7 to about 8. In some embodiments, the micelles have a pH transition value of about 6.3 to about 6.9. In some embodiments, the micelles have a pH transition value of about 5.0 to about 6.2. In some embodiments, the micelles have a pH transition value of about 5.9 to about 6.2. In some embodiments, the micelles have a pH transition value of about 5.0 to about 5.5. In some embodiments, the micelles have a pH transition value of about 6.3 to about 7.2. In some embodiments, the micelles have a pH transition value of about 5.0 to about 6.5. In some embodiments, the micelles have a pH transition value of about 6.2 or above 6.2. In some embodiments, the micelles have a pH transition value of about 5.5.

Therapeutic Methods and Kits

The micelles may be formulated into compositions suitable for administration to an individual by combining a micelle as described herein with a pharmaceutically acceptable carrier. Also provided by the invention are kits comprising (i) a container comprising a micelle as described herein and (ii) instructions for use in a method of treating a cancer. The kit may further comprise a pharmaceutically acceptable carrier.

The micelles of the invention are useful in treating cancer. In some embodiments, the cancer comprises a solid tumor. In some embodiments, the cancer is a non-solid cancer. Examples of cancers which may be treated include non-small cell lung cancer, breast cancer, prostate cancer, and pancreatic cancer, which have elevated expressions of NQO1 enzymes.

The micelle formulations may be administered to the individual by any suitable method, such as, for example, intravenous injection or infusion.

The following examples are provided for illustrative purposes only and are not intended to limit the scope of the invention in any manner. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

Materials

All solvents and reagents were of analytical or HPLC grade and purchased from Sigma-Aldrich or Fisher Scientific unless otherwise stated. Deuterated solvents were from Sigma. The 2-(diisopropylamino) ethyl methacrylate was recrystallized from ethyl acetate prior to use. Poly(ethylene glycol) methyl ether (mPEG-5000, Mn 5000) was purchased from Sigma Aldrich and purified before use by passing through a column filled with neutral alumina. Copper(II) bromide (CuBr2, 99%), 2-bromo-2-methylpropionyl bromide, N,N,N',N'',N'''-Pentamethyldiethylenetriamine (PMDETA, 98%), p-Toluenesolfonic acid monohydrate (TsOH, 98%), 5-amino-1-pentanol (98%), 4-amino-2-methyl-phenol (98%), acylhydrazine (98%), N-(4-Aminophenyl)maleimide (Mal, TCI America, 95%), Tris(2-carboxyethyl) phosphine hydrochloride (TCEP), 2-(diisopropylamino) ethyl methacrylate (DPA, TCI America, 99%), dialysis membrane (MWCO 3500, regenerated cellulose) were used as received from Fisher. β-Lapachone (β-Lap) was synthesized from lapachol following a previously reported procedure (Elvin Blanco, E. A. B., Ying Dong, Brent D. Weinberg, Damon M. Sutton, David A. Boothman, Jinming Gao. (2007) β-Lapachone-containing PEG-PLA polymer micelles as novel nanotherapeutics against NQO1-overexpressing tumor cells. J. Controlled. Release 122, 365-374).

Example 1

Design and Synthesis of Aminoalkyl Alcohol Prodrugs

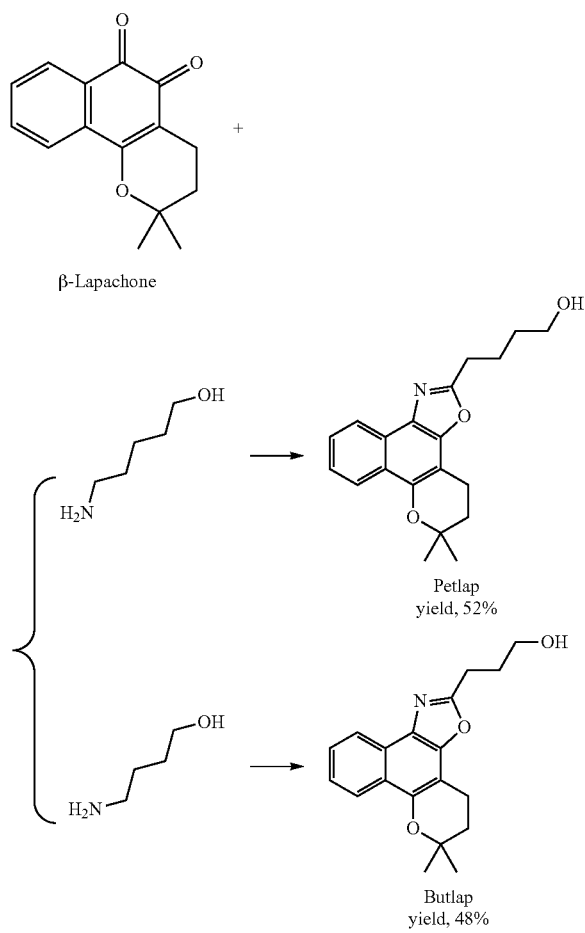

Synthesis of Petlap (4-(6,6-dimethyl-5,6-dihydro-4H-benzo[7,8]chromeno[6,5-d]oxazol-2-yl)butan-1-ol (4))

β-Lap (100 mg, 0.41 mmol), 5-amine-1-pentanol (46.8 mg, 0.45 mmol) and 100 μL HOAc with 5 mL of anhydrous methanol were refluxed in a single neck flask for 24 hrs, then the solvent was removed under vacuum, and the residue dissolved in 30 mL of EtOAc, washed with saturated NaHCO$_3$ aqueous solution 3 times, then washed with saturated NaCl aqueous solution for 3 times, dried with MgSO$_4$ overnight, and the crude product separated by silicone gel chromatography with eluent of Hexane/EtOAc=4:1. 53.5 mg (4) was obtained. MS: 326.1[M+H]$^+$, $^1$HNMR (500 MHz, CDCl$_3$) δ: 8.325-8.309 (1H, d, J=8.0), 8.269-8.253 (1H, d, J=8.0), 7.578-7.548 (1H, t, J=7.5), 7.465-7.435 (1H, t, J=7.5), 3.725-3.701 (2H, t, J=6.0 Hz), 3.051-2.992 (4H, m), 2.064-2.005 (2H, m), 1.966-1.940 (2H, t, J=6.5), 1.771-1.716 (2H, m), 1.449 (6H, s). $^{13}$CNMR (125 MHz, CDCl$_3$) δ: 164.5 (1C), 147.8 (1C), 147.3 (1C), 126.9 (1C), 125.2 (1C), 124.4 (1C), 123.9 (1C), 122.8 (1C), 121.8 (1C), 105.0 (1C), 102.0 (1C), 75.3 (1C), 62.2 (1C), 32.4 (1C), 32.0 (1C), 28.6 (1C), 26.9 (2C), 23.5 (1C), 17.6 (1C).

Synthesis of Butlap (4-(6,6-dimethyl-5,6-dihydro-4H-benzo[7,8]chromeno[6,5-d]oxazol-2-yl)propan-1-ol)

Briefly, 100 mg (0.41 mmol) β-Lapachone, 0.45 mmol 4-amino-1-butanol, and 100 μL HOAc with 5 mL of anhydrous methanol were refluxed in a single neck flask for 24 hrs, then the solvent was removed under vacuum, the residue dissolved in 10 mL of EtOAc, washed with saturated NaHCO$_3$, aqueous solution 3 times, then washed with 5 mL saturated NaCl aqueous solution 3 times, and dried with MgSO$_4$ overnight. The compounds were separated by silicon gel chromatography, with eluent of Hexane: EtOAc=4:1. Butlap: MS: 312 [M+H]$^+$, $^1$HNMR (500 MHz, CDCl$_3$) δ: 8.321-8.304 (1H, d), 8.276-8.259 (1H, d), 7.579-7.549 (1H, t), 7.470-7.436 (1H, t, J=1.5), 3.846-3.822 (2H, t, J=6.0 Hz), 3.154-3.126 (2H, t, J=7.0), 3.007-2.979 (2H, t, J=7.0), 2.204-2.153 (2H, m), 1.960-1.9451 (2H, t), 1.416 (6H, s). $^{13}$CNMR (125 MHz, CDCl$_3$) δ: 164.4 (1C), 147.8 (1C), 147.4 (1C), 126.89 (1C), 125.2 (1C), 124.5 (2C), 123.9 (1C), 122.8 (1C), 121.7 (1C), 102.0 (1C), 75.3 (1C), 62.2 (1C), 32.0 (1C), 30.0 (1C), 26.9 (2C), 26.1 (1C), 17.6 (1C).

Example 2

Design and Synthesis of Acetyl Hydrazone Prodrug

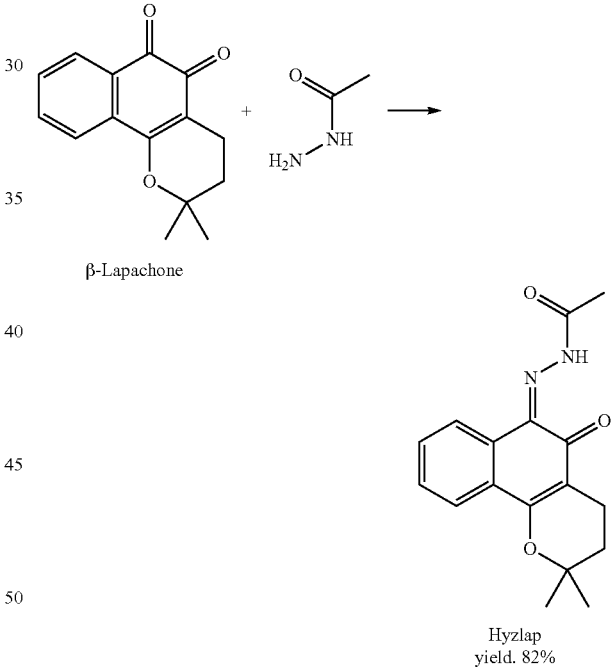

Synthesis of Hyzlap ((Z)—N'-(2,2-dimethyl-5-oxo-3,4-dihydro-2H-benzo[h]chromen-6(5H)-ylidene)acetohydrazide (1))

Hyzlap was synthesized using the same method as in Example 1 (Petlap). Yield, 82%, MS: 299.1 [M+H]$^+$, $^1$HNMR (500 MHz, CDCl$_3$) δ: 8.162-8.159 (1H, d, J=1.5), 7.879-7.867 (1H, d, J=6.0), 7.491-7.427 (2H, m), 2.643-2.497 (5H, m), 1.864-1.839 (2H, t, J=6.0), 1.661 (1H, s), 1.450 (6H, s). $^{13}$CNMR (125 MHz, CDCl$_3$) δ: 181.7 (1C), 175.5 (1C), 162.2 (1C), 132.0 (1C), 130.2 (1C), 128.9 (1C), 127.2 (1C), 123.5 (3C), 111.7 (1C), 78.8 (1C), 31.9 (1C), 27.0 (2C), 20.1 (1C), 16.2 (1C).

Example 3

Design and Synthesis of Amino Aromatic Phenol Prodrugs

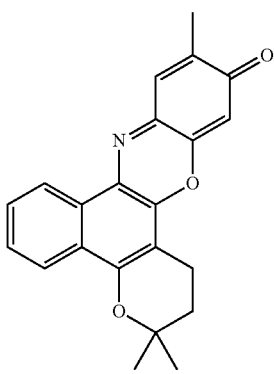 [SMILES: Cc1cc2nc3c(oc-2cc1=O)c1c(c2ccccc23)OC(C)(C)CC1]

3,3,11-trimethyl-2,3-dihydrobenzo[a]pyrano[2,3-c]phenoxazin-12(1H)-one (5) was synthesized using the same method as in Example 1 (Petlap). Yield, 27.1%, MS: 346.1 [M+H]$^+$, $^1$HNMR (500 MHz, CDCl$_3$) δ: 8.819-8.803 (1H, d, J=8.0 Hz), 8.248-8.23 (1H, d, J=8.0 Hz), 7.723-7.709 (1H, t, J=7.5 Hz), 7.589-7.559 (1H, t, J=7.5 Hz), 6.763-6.766 (1H, d, 1.0 Hz), 6.361-6.357 (1H, d, 2 Hz), 3.014-2.988 (2H, t, J=6.5 Hz), 2.577 (3H, s), 2.026-1.999 (2H, t, J=6.5 Hz), 1.512 (6H, s). $^{13}$CNMR (125 MHz, CDCl$_3$) δ: 185.9 (1C), 155.7 (1C), 151.5 (1C), 143.6 (1C), 143.0 (1C), 142.5 (1C), 132.3 (1C), 132.2 (1C), 130.9 (1C), 129.3 (1C), 128.3 (1C), 124.0 (1C), 123.1 (1C), 122.2 (1C), 105.1 (1C), 104.8 (1C), 78.3 (1C), 31.4 (1C), 26.9 (2C), 16.4 (2C).

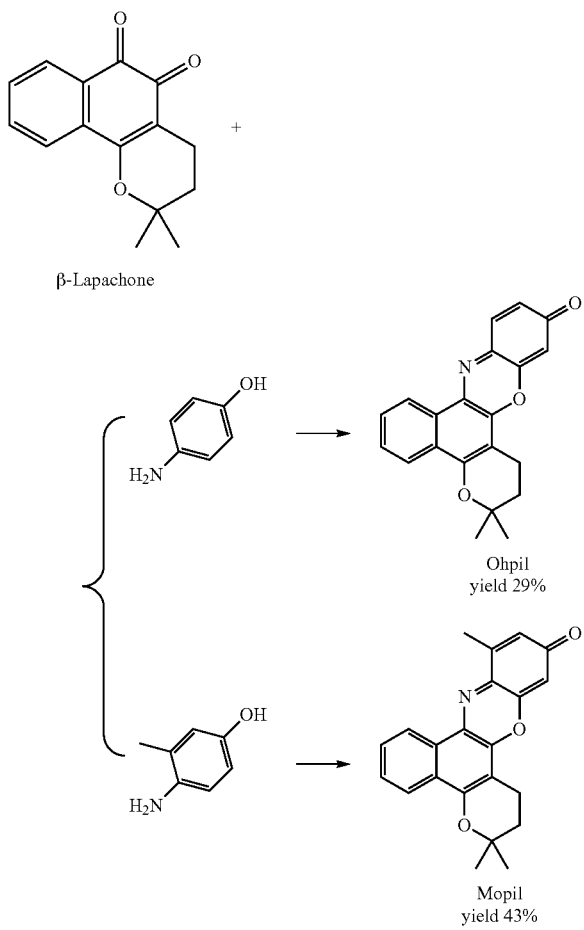

Ohpil, Mopil, and Eapil were synthesized according to the following method. Briefly, 100 mg (0.41 mmol) β-Lapachone, 0.45 mmol 4-amine-phenol (Ohpil), 4-amino-3-methyl-phenol (Mopil), or 2-(4-aminophenoxy)ethanol (Eapil), and 100 μL HOAc with 5 mL of anhydrous methanol were refluxed in a single neck flask for 24 hrs, then the solvent was removed under vacuum, the residue dissolved in 10 mL of EtOAc, washed with saturated NaHCO$_3$ aqueous solution 3 times, then washed with saturated NaCl aqueous solution for 5 mL×3 times, and dried with MgSO$_4$ overnight. The compounds were separated by silicon gel chromatography, with eluent of Hexane: EtOAc=4:1.

Ohpil (3,3-dimethyl-2,3,13,13a-tetrahydrobenzo[a]pyrano[2,3-c]phenoxazin-12(1H)-one)

MS: 332 [M+H]$^+$, $^1$HNMR (500 MHz, CDCl$_3$) δ: 8.795-8.777 (1H, d, J=9.0), 8.225-8.207 (1H, d, J=9.0), 7.690-7.671 (1H, m), 7.596-7.552 (2H, m), 6.909-6.885 (1H, dd, J=2.5 Hz, 2.0 Hz), 6.434 (1H, s), 3.005-2.978 (2H, t), 2.007-1.977 (2H, t), 1.486 (6H, s). $^{13}$CNMR (125 MHz, CDCl$_3$) δ: 186.2 (1C), 156.3 (1C), 150.9 (1C), 143.8 (1C), 142.1 (1C), 134.5 (1C), 133.6 (1C), 130.4 (1C), 129.2 (1C), 128.1 (1C), 126.8 (1C), 124.2 (1C), 122.4 (1C), 116.7 (1C), 105.9 (1C), 104.9 (1C), 73.9 (1C), 31.6 (1C), 27.0 (2C), 16.8 (1C).

Mopil (3,3,11-trimethyl-2,3,13,13a-tetrahydrobenzo[a]pyrano[2,3-c]phenol-xazin-12(1H)-one)

MS: 346.1 [M+H]$^+$, $^1$HNMR (500 MHz, CDCl$_3$) δ: 8.813-8.797 (1H, d, J=8.0 Hz), 8.243-8.226 (1H, d, J=8.5 Hz), 7.717-7.687 (1H, t, J=7.0 Hz), 7.583-7.553 (1H, t, J=8.0 Hz), 6.763 (1H, s), 6.355 (1H, s), 3.008-2.982 (2H, t, J=7.0 Hz), 2.571 (3H, s), 2.019-1.993 (2H, t, J=6.5 Hz), 1.506 (6H, s). $^{13}$CNMR (125 MHz, CDCl$_3$) δ: 185.9 (1C), 155.7 (1C), 151.5 (1C), 143.6 (1C), 143.0 (1C), 142.5 (1C), 132.3 (1C), 132.2 (1C), 130.9 (1C), 129.3 (1C), 128.3 (1C), 124.0 (1C), 123.1 (1C), 122.2 (1C), 105.1 (1C), 104.8 (1C), 78.3 (1C), 31.4 (1C), 26.9 (2C), 16.4 (2C).

Eapil ((E)-6-(4-(2-hydroxyethoxy)phenyl)imino)-2,2-dimethyl-3,4-dihydro-2H-benzo[h]chromen-5(6H)-one)

Yield, 40%, MS: 378.2 [M+H]$^+$, $^1$HNMR (500 MHz, CDCl$_3$) δ: 7.583 (m, 1H), 7.332 (m, 1H), 7.236 (m, 2H), 7.204 (d, 2H, J=4.8 Hz), 6.855 (d, 2H, J=4.8 Hz), 4.033 (t, 2H, J=6.8 Hz), 3.853 (t, 2H, J=6.8 Hz), 1.993 (t, 2H, J=5.6 Hz), 1.878 (t, 2H, J=5.6 Hz), 1.395 (s, 6H).

Example 4

Design and Synthesis of Ketal Linker Prodrugs

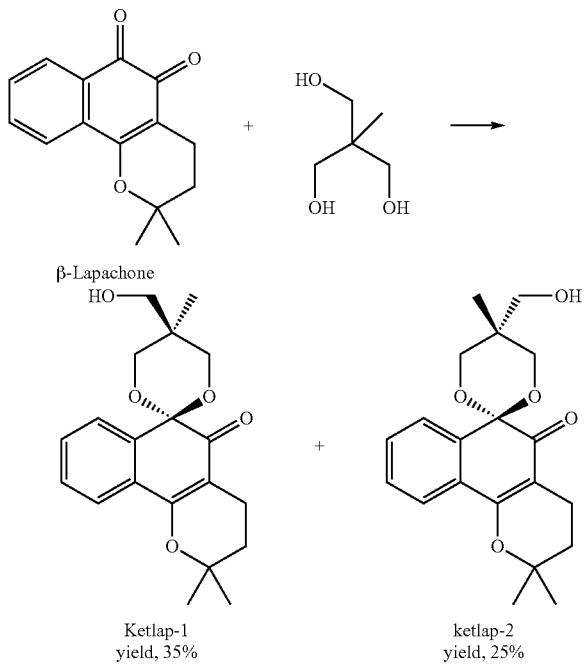

Synthesis of Ketlap-1 ((2'r,5'r)-5'-(hydroxymethyl)-2,2,5'-trimethyl-3,4-dihydrospiro[benzo[h]chromene-6,2'-[1,3]dioxan]-5(2H)-one (2)) and Ketlap-2 (2's,5's)-5'-(hydroxymethyl)-2,2,5'-trimethyl-3,4-dihydrospiro[benzo[h]chromene-6,2'-[1,3]dioxan]-5(2H)-one (3)

(See Griset, A. P., Walpole, J., Liu, R., Gaffey, A., Colson, Y. L., and Grinstaff, M. W. (2009) Expansile nanoparticles: synthesis, characterization, and in vivo efficacy of an acid-responsive polymeric drug delivery system. J. Am. Chem. Soc. 131, 2469-2471). β-Lap (94.2 mg, 0.389 mmol), 1,1,1-Trimethanolethane 2-(Hydroxymethyl)-2-methyl-1,3-propanediol (140 mg, 1.17 mmol) and p-toluenesulfonic acid (10.3 mg, 0.054 mmol) were added into 15 mL of anhydrous benzene in a single neck flask, decorated with a Dean-Stark trap, and the reaction kept refluxing for 48 hrs. The benzene was removed under vacuum, the residue dissolved in 30 mL EtOAc, the organic phase washed with saturated NaHCO$_3$ aqueous solution for 3 times, then washed with saturated NaCl aqueous solution 3 times, dried with MgSO$_4$ overnight, and the products separated by silicone gel chromatography with eluent Hexane/EtOAc=6:1, mostly β-Lap was recovered, and 25.7 mg (2) and 15.3 mg (3) were obtained.

(2'r,5'r)-5'-(hydroxymethyl)-2,2,5'-trimethyl-3,4-dihydrospiro[benzo[h]chromene-6,2'-[1,3]dioxan]-5(2H)-one (2)

MS: 345.1[M+H]$^+$, $^1$HNMR (500 MHz, CDCl$_3$) δ: 7.805-7.787 (1H, dd, J=1.5, 1.0), 7.729-7.711 (1H, dd, J=1.0, 1.5), 7.445-7.412 (1H, ddd, J=1.5, 1.5, 1.5), 7.385-7.352 (1H, ddd, J=1.5, 1.5, 1.5), 4.596-4.572 (2H, d, J=12.0), 3.994 (2H, s), 3.771-3.747 (2H, d, J=12.0), 2.442-2.416 (2H, t, J=6.5), 1.793-1.767 (2H, t, J=6.5), 1.392 (6H, s), 0.851 (3H, s). $^{13}$CNMR (125 MHz, CDCl$_3$) δ: 194.3 (1C), 160.5 (1C), 139.0 (1C), 130.6 (1C), 129.4 (2C), 128.3 (1C), 127.2 (1C), 123.5 (1C), 105.0 (1C), 89.5 (1C), 67.4 (1C), 66.1 (2C), 34.7 (1C), 32.0 (1C), 26.9 (2C), 17.6 (1C), 16.0 (1C).

(2's,5's)-5'-(hydroxymethyl)-2,2,5'-trimethyl-3,4-dihydrospiro[benzo[h]chromene-6,2'-[1,3]dioxan]-5(2H)-one (3)

MS: 345.1 [M+H]$^+$, $^1$HNMR (500 MHz, CDCl$_3$) δ: 7.899-7.881 (1H, dd, J=1.5, 1.5), 7.741-7.723 (1H, dd, J=1.5, 1.5), 7.473-7.440 (1H, ddd, J=1.0, 1.0, 1.5), 7.398-7.365 (1H, ddd, J=1.5, 1.0, 1.5), 4.757-4.735 (2H, d, J=11.0), 3.619-3.597 (2H, d, J=11.0), 3.467 (2H, s), 2.440-2.414 (2H, t, J=6.5), 1.794-1.768 (2H, t, J=6.5), 1.445 (3H, s), 1.396 (6H, s). $^{13}$CNMR (125 MHz, CDCl$_3$) δ: 194.1 (1C), 161.3 (1C), 139.2 (1C), 130.5 (1C), 129.5 (2C), 128.3 (1C), 127.3 (1C), 123.4 (1C), 105.1 (1C), 89.6 (1C), 67.3 (1C), 66.2 (2C), 34.7 (1C), 32.1 (1C), 26.8 (2C), 17.5 (1C), 16.1 (1C).

The Absolute Structure Conformation for (2) and (3)

The $^1$HNMR chemical shift of (2) and (3) were different for several protons, due to different spatial conformation. 1D-NOE were performed on a Varian 500 MHz NMR Spectrometer to confirm the absolute configuration of (2) and (3).

Example 5

Design and Synthesis of Amino Aromatic Alcohol Prodrugs

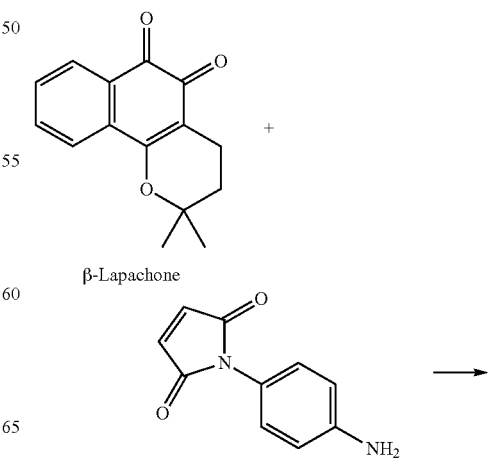

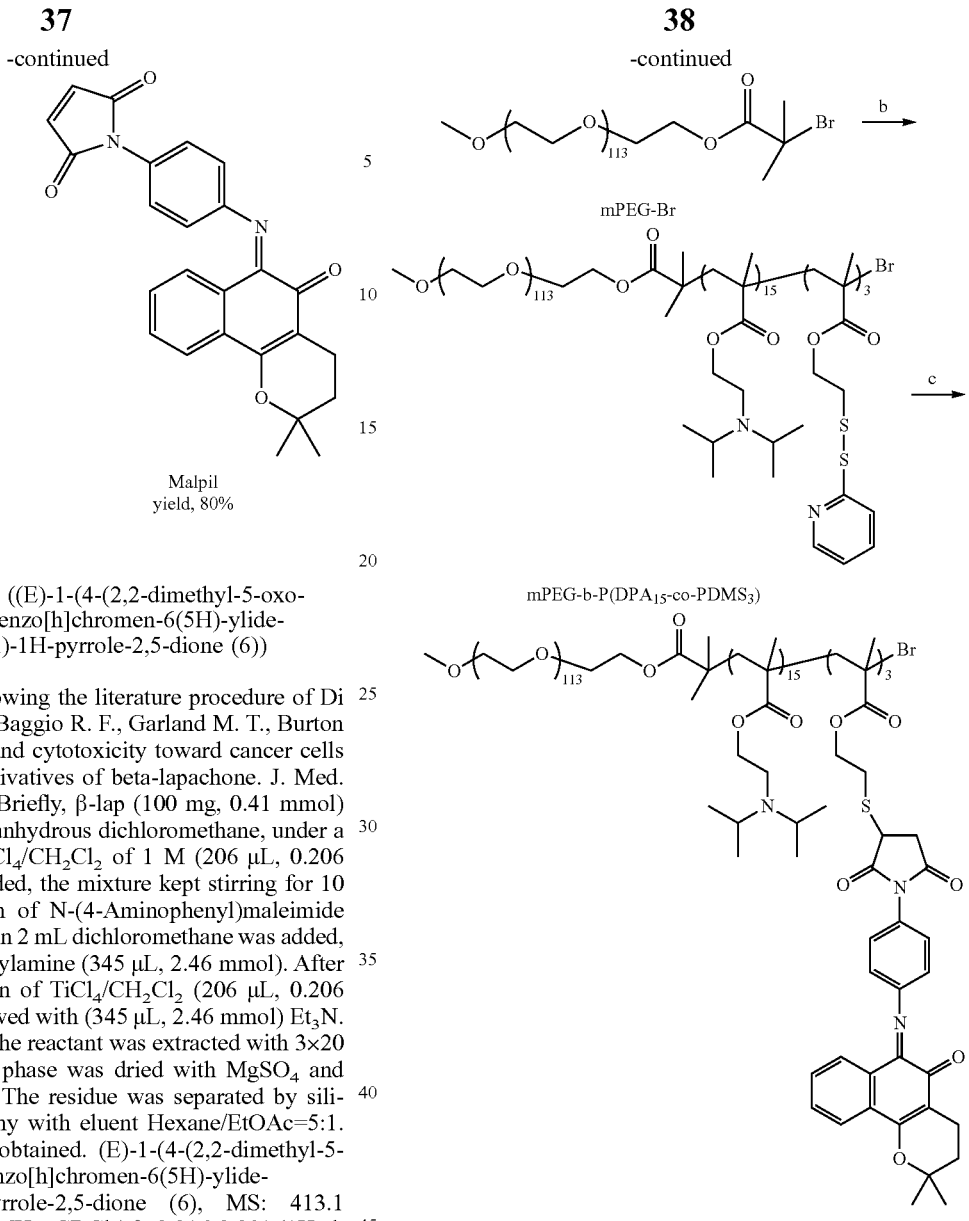

mPEG-Br mPEG-b-P(DPA$_{15}$-co-PDMS$_3$)

mPEG-b-P(DPA$_{15}$-co-PDMS(6)$_3$)

a) CH$_2$Cl$_2$, Et$_3$N, 2-bromoisobutylryl-bromide;
b) PDMEDTA, CuBr, isopropanol, DMF, Anisole, 65° C.
c) TECP, (6)

Malpil
yield, 80%

Synthesis of Malpil ((E)-1-(4-(2,2-dimethyl-5-oxo-3,4-dihydro-2H-benzo[h]chromen-6(5H)-ylideneamino)phenyl)-1H-pyrrole-2,5-dione (6))

was synthesized following the literature procedure of Di Chema P. H., B.-D. V., Baggio R. F., Garland M. T., Burton G. (2001) Preparation and cytotoxicity toward cancer cells of mono(arylimino) derivatives of beta-lapachone. J. Med. Chem. 44, 2486-2489. Briefly, β-lap (100 mg, 0.41 mmol) was dissolved in 3 mL anhydrous dichloromethane, under a dry Ar atmosphere, TiCl$_4$/CH$_2$Cl$_2$ of 1 M (206 μL, 0.206 mmol) solution was added, the mixture kept stirring for 10 mins, then the solution of N-(4-Aminophenyl)maleimide (77.75 mg, 0.41 mmol) in 2 mL dichloromethane was added, followed with dry triethylamine (345 μL, 2.46 mmol). After 15 mins another portion of TiCl$_4$/CH$_2$Cl$_2$ (206 μL, 0.206 mmol) was added followed with (345 μL, 2.46 mmol) Et$_3$N. After another 15 mins, the reactant was extracted with 3×20 mL H$_2$O. The CH$_2$Cl$_2$ phase was dried with MgSO$_4$ and evaporated in vacuum. The residue was separated by silicone gel chromatography with eluent Hexane/EtOAc=5:1. 123.6 mg Malpil was obtained. (E)-1-(4-(2,2-dimethyl-5-oxo-3,4-dihydro-2H-benzo[h]chromen-6(5H)-ylideneamino)phenyl)-1H-pyrrole-2,5-dione (6), MS: 413.1 [M+H]$^+$, $^1$HNMR (500 MHz, CDCl$_3$) δ: 8.216-8.201 (1H, d, J=7.5), 7.838-7.822 (1H, d, J=8.0), 7.552-7.490 (2H, m), 7.335-7.318 (2H, d, J=7.5), 6.829-6.804 (4H, m), 2.426-2.400 (2H, t, J=6.5), 1.804-1.777 (2H, t, J=7.0), 1.438 (6H, s). $^{13}$CNMR (125 MHz, CDCl$_3$) δ: 177.7 (1C), 170.0 (2C), 161.8 (1C), 152.9 (1C), 134.4 (2C), 132.7 (1C), 131.6 (1C), 130.5 (2C), 130.3 (1C), 127.3 (1C), 126.6 (2C), 126.2 (1C), 123.6 (1C), 116.7 (2C), 112.2 (1C), 78.8 (1C), 32.0 (1C), 27.0 (2C), 16.3 (1C).

Example 6

Synthesis of mPEG-b-P(DPA$_{15}$-co-PDMS (6)$_3$)

Scheme 4. Synthetic route of polymer mPEG-b-P(DPA$_{15}$-co-PDMS(6)$_3$):

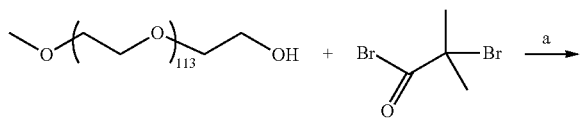

Synthesis of mPEG-Br and PDMS.

(Wang, J. S., and Matyjaszewski, K. (1995) Controlled Living Radical Polymerization—Atom-Transfer Radical Polymerization in the Presence of Transition-Metal Complexes. J. Am. Chem. Soc. 117, 5614-5615; Kato, M., Kamigaito, M., Sawamoto, M., and Higashimura, T. (1995) Polymerization of Methyl-Methacrylate with the Carbon-Tetrachloride Dichlorotris(Triphenylphosphine) Ruthenium (Ii) Methylaluminum Bis(2,6-Di-Tert-Butylphenoxide) Initiating System—Possibility of Living Radical Polymerization. Macromolecules 28, 1721-1723). mPEG-OH (10 g, 2 mmol) was dissolved in 100 mL of toluene in a round bottom flask with a Dean-Stark Trap, and refluxed at 140° C. for 3 hours to remove H$_2$O. After the toluene was distilled off under vacuum, anhydrous CH$_2$Cl$_2$ (125 mL) and Et$_3$N (0.55 mL, 8 mmol) were added to the residue, then 2-bromoisobutylryl-bromide (1 mL, 8 mmol) in 30 mL CH$_2$Cl$_2$ was added drop wise over 2 hours under nitrogen atmosphere. After 24 hours, 2 mL water was added into the vigorously stirring solution, then washed with 1M HCl aqueous solution, 1M NaOH and saturated NaCl solution each for 3 times individually. The mixture was dried overnight with MgSO$_4$, condensed and dropped into 800 mL ethyl ester 3 times. 7.2 g of a white solid was obtained, yield 69.7% (Scheme 4-a). PDMS (2-(2-pyridyldisulfide) ethylmethacrylate) monomer was synthesized according the literature (Ghosh, S., Basu, S., and Thayumanavan, S. (2006) Simultaneous and reversible functionalization of copolymers for biological applications. Macromolecules 39, 5595-5597, Jia, Z., Wong, L., Davis, T. P., and Bulmus, V. (2008) One-pot conversion of RAFT-generated multifunctional block copolymers of HPMA to doxorubicin conjugated acid- and reductant-sensitive crosslinked micelles. Biomacromolecules 9, 3106-13).

Synthesis of mPEG-b-P(DPA-co-PDMS).

(Ghosh, S., Basu, S., and Thayumanavan, S. (2006) Simultaneous and reversible functionalization of copolymers for biological applications. Macromolecules 39, 5595-5597). mPEG-Br (300 mg, 0.6 mmol), DPA (2-(diisopropylamino) ethyl methacrylate) (256.6 mg, 12 mmol), PDMS (56.2 mg, 3.0 mmol), and PMDETA (N,N,N',N'',N'''-pentamethyldiethylenetriamine) (21 mg, 1.2 mmol) were dissolved in a mixture of 0.2 mL anisole, 0.3 mL DMF and 0.3 mL isopropanol. After freezing-thaw 3 times in liquid nitrogen, CuBr (8.6 mg, 0.6 mmol) was added under N$_2$ atmosphere, and the reaction kept stirring at 65° C. for 24 hrs. The reaction was quenched with liquid nitrogen and the Cu complexes removed with a short neutral Aluminum oxide column with TI-IF as eluent, followed by dialysis against DI water for 2 days and further purification by centrifuge device (MWCO 10000), then freezing dry to obtain 341 mg block copolymer. $^1$HNMR showed there were about 15 DPA and 3 PDMS in the polymer chain, yield 55.7% (Scheme 4-b).

Synthesis of mPEG-b-P(DPA-co-PDMS (6))

(Gijs J. M. Habraken, C. E. K., Johan P. A. Heuts, Andreas Heise. (2009) Thiol chemistry on well-defined synthetic polypeptides. Chem. Comm., 24, 3612-3614). mPEG-b-P(DPA-co-PDMS) (46.2 mg, 4.68 µmol) was dissolved in 1 mL of anhydrous DMF, then TCEP (tris(2-carboxyethyl) phosphine hydrochloride) (8.4 mg, 29.3 µmol) in 0.2 mL pH 8.4 citric acid-KH$_2$PO$_4$ buffer was added. After 0.5 hrs Malpil prodrug (6) (9.2 mg, 22.3 µmol) was added, the reaction kept stirring for 24 hrs, then the reaction was poured into 20 mL DI water, the free small molecules removed by centrifugation with MWCO 3,000 filter device and washed with DI water, then freezing dry to get 45 mg polymer. Yield 88.5%, $^1$HNMR showed three Malpil prodrug (6) were conjugated into the polymer chain (Scheme 4c). mPEG-b-P(DPA-co-PDMS (6)) having approximately 15 DPA and 3 PDMS was used in the following Example 8 below.

To achieve polymeric micelles which can maintain micelle integrity in neutral pH, and dissociate at acidic pH, the monomer 2-(diisopropylamino) ethyl methacrylate (DPA, pKa 6.5) bearing amino groups was incorporated into polymers as ionizable groups to render pH sensitivity (Butun, V., Armes, S. P., and Billingham, N. C. (2001) Synthesis and aqueous solution properties of near-monodisperse tertiary amine methacrylate homopolymers and diblock copolymers. Polymer 42, 5993-6008; Kim, M. S., Hwang, S. J., Han, J. K., Choi, E. K., Park, H. J., Kim, J. S., and Lee, D. S. (2006) pH-responsive PEG-poly(beta-amino ester) block copolymer micelles with a sharp transition. Macromol. Rapid Commun. 27, 447-451). In order to load β-lap prodrug (6) into the polymer chain by conjugation, a monomer of 2-(pyridin-2-yldisulfanyl)ethyl methacrylate (PDMS) was also introduced into the polymer. The loading efficiency of β-lap was determined by the number of PDMS in the polymer chain. Block copolymer mPEG-b-P(DPA$_{15}$-co-PDMS$_3$) was acquired by using mPEG-Br as macromolecular initiator, DPA and PDMS as monomers in a certain mole ratio which were polymerized by Atom transfer radical polymerization(ATRP). The number of DPA and PDMS was determined by $^1$HNMR spectrum. By defining mPEG proton as 450, there were about 15 DPA and 3 PDMS introduced into the hydrophobic segment. High efficient conjugation of prodrug (6) was performed by thioene addition after removal of the protecting thiol-pyridine group. $^1$HNMR in CDCl$_3$ showed the three thiol groups were all reacted with the double bond in Maleic structure of (6). Proton assignment of $^1$HNMR on polymer mPEG-b-P(DPA-co-PDMS) polymer and drug loaded polymer mPEG-b-P(DPA-co-PDMS (6)) indicated the successful conjugation of prodrug (6). The number of prodrug (6) on mPEG-b-P(DPA-co-PDMS (6)) was also calculated by HPLC analysis (Data not shown), by incubating polymer mPEG-b-P(DPA-co-PDMS (6)) micelles under pH 1.0 HCl solution for 6 hrs. The polymer system loading efficiency reached 7.4% by weight, which was much higher than by encapsulation method.

In a similar manner using different molar ratios of reactants, mPEO$_{114}$-b-P(DPA$_{12}$-co-PDMS$_{4.6}$) and mPEG$_{114}$-b-P(DPA$_{12}$-co-PDMS (Malpil)$_3$-co-PDMS) was obtained.

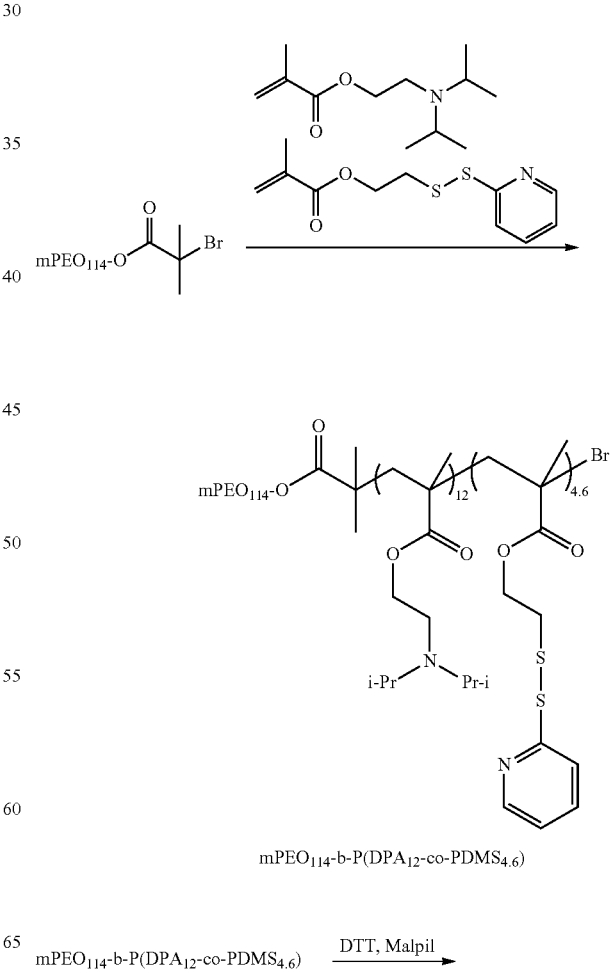

mPEO$_{114}$-b-P(DPA$_{12}$-co-PDMS$_{4.6}$)

mPEO$_{114}$-b-P(DPA$_{12}$-co-PDMS$_{4.6}$) $\xrightarrow{\text{DTT, Malpil}}$

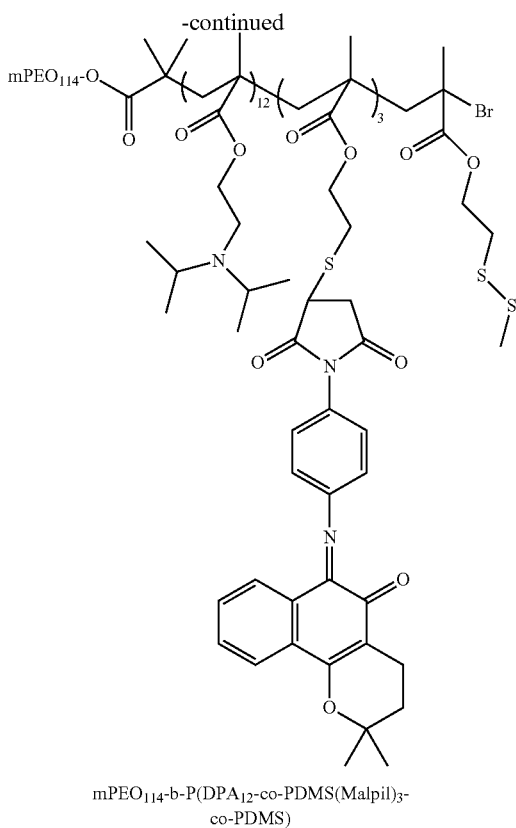

mPEO$_{114}$-b-P(DPA$_{12}$-co-PDMS(Malpil)$_3$-co-PDMS)

Example 7

Synthesis of Polymers mPEG-PCys(Malpil)

Synthesis of mPEG-P(Cys(Malpil))$_8$. The following reaction was performed to obtain a product having n=8 (see FIG. 8):

216 mg mPEG5k-NH$_2$ was dissolved in 2 mL of dry DMF and was added to a solution of 97.2 mg t-butyl protected Cysteine-NCA (N-carboxyanhydride) in 2 mL of dry DMF under the protection of nitrogen. One drop of triethylamine was added into the mixture. After 3 days stirring at 35° C., the reaction solution was poured into 50 mL ethyl ether and the precipitates were collected through centrifugation. After drying the precipitates in vacuum, 249 mg of product (mPEG-P(Cys(t-Bu))$_8$) was obtained as a white powder.

100 mg of mPEG-P(Cys(t-Bu))$_8$ and 160 mg DTT was dissolved in 2 mL DMF and stirred at 60° C. for 4 hours. The reaction mixture was poured into 100 mL DI water and centrifuged. After drying in vacuum, 55 mg of product (mPEG-PCys$_8$) was obtained as a white powder.

50 mg of mPEG-PCys$_8$. 8.4 mg Malpil and 3.4 mg AIBN (Azobisisobutyronitrile) was dissolved in 3 mL DMF and stirred at 60° C. After 1 hour's stirring, the reaction mixture was precipitated in ethyl ether twice. After drying in vacuum, 56 mg product mPEG-P(Cys(Malpil))$_8$ was obtained as a white powder.

Figure 8:
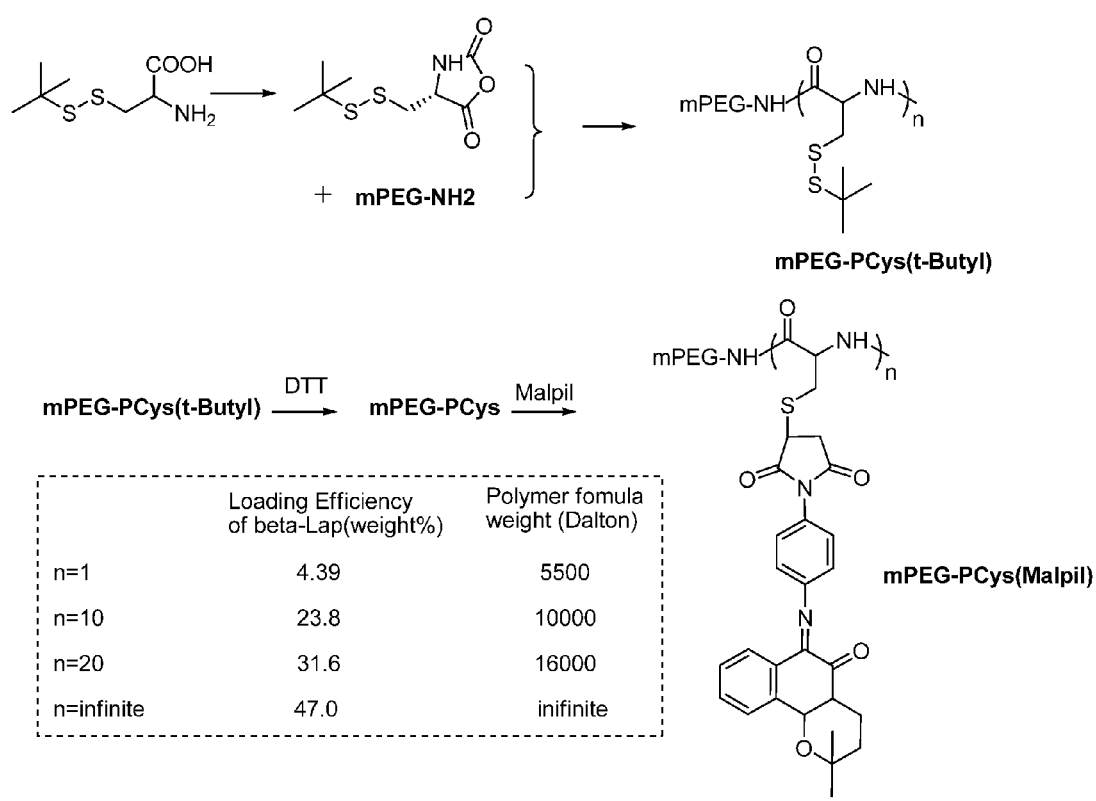
FIG. 8 illustrates synthesis of mPEG-P(Cys(Malpil)) polymers.

A similar reaction is performed to obtain products having n=1, 5, 10, and 20. The polymer formula weights and loading efficiency of beta-lap for products having n=1, 10, 20 is shown in FIG. 8.

Example 8 mPEG$_{114}$-b-P(DPA$_{15}$-co-PDMS (6)$_3$) Micelles

Introduction

In this study, we designed a dual pH sensitive polymer system in which: (1) the polymeric micelles maintained integrity in blood stream pH, and disassociated when exposed to endosomal/lysosomal pH, accompanied by protonation of the hydrophobic segment, and (2) released conjugated drug from the prodrug in a pH-sensitive manner. We hypothesized that dual pH-sensitive polymeric micelles would allow for a high drug loading density of beta-lap in the micelles at neutral pH, while providing a pH-sensitive drug release at the acidic endosomal/lysosomal pH inside tumor cells.

Several β-Lap prodrugs and analogues were synthesized with different types of linkers including ketal linker (see (2) and (3) in Example 4), acylhydrazone linker (see (1) in Example 2), and imine linkers (see (6) in Example 5). A hydrolysis study at neutral pH and acidic pH indicated that the ketal and acylhydrazone prodrugs (1, 2, 3) were not pH-sensitive within biological and endosomal/lysosomal pH range, and not good candidates for pH sensitive β-Lap delivery. In addition, the oxazole ring in (4) or oxazin in (5) resisted acid catalyzed hydrolysis (data not shown). Prodrug (6) showed, inspiring pH sensitivity both at neutral and at acidic conditions.

Figure 4:
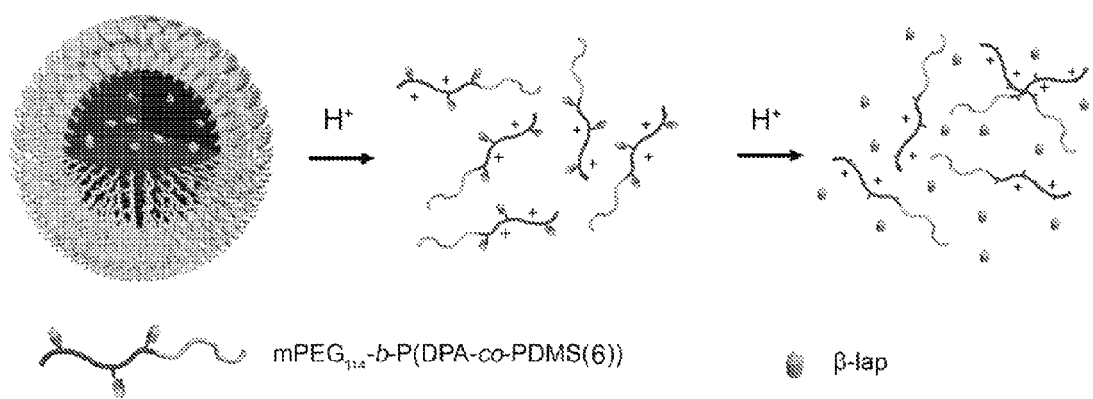
FIG. 4 is a schematic illustration of pH-sensitive micelle dissociation and beta-lapachone release from a polymeric micelle. At acidic conditions, the micelles will first disassociate into unimer, followed by cleavage of beta-lap from the co-polymer.
Figure 5:
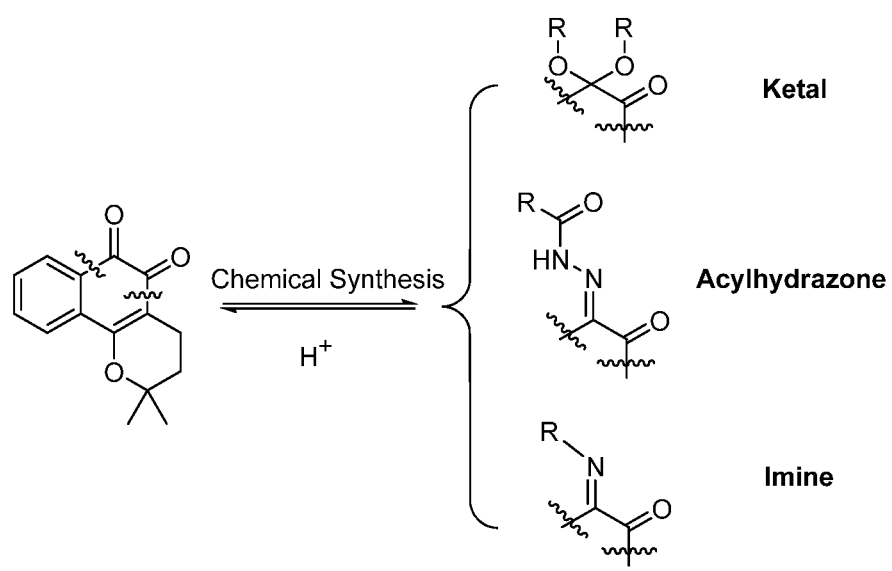
FIG. 5 is a schematic of various β-Lap prodrug structures.
Figure 6:
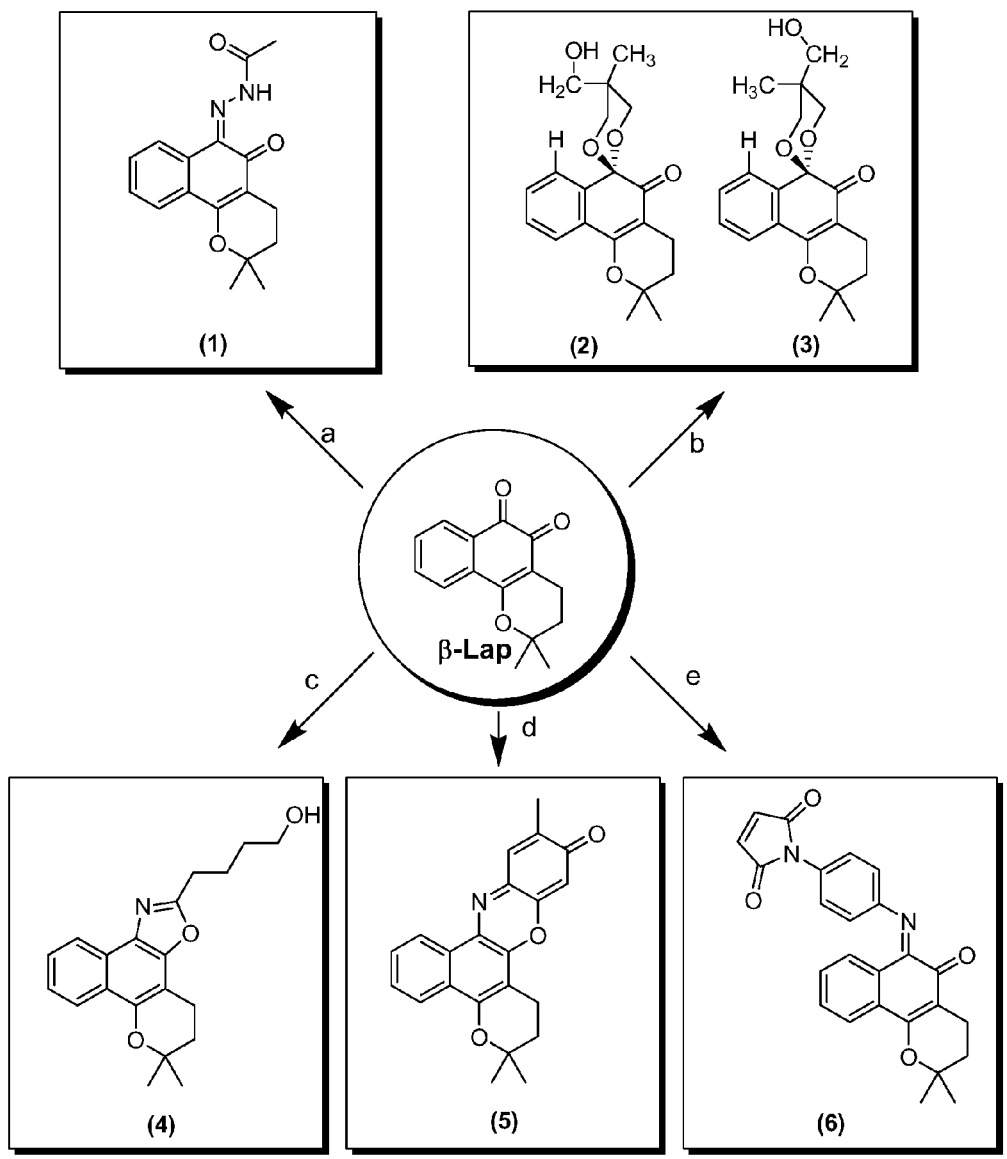
FIG. 6 is shows syntheses of different 3-lap prodrugs: a) acetohydrazide, TsOH; b) 2-(hydroxymethyl)-2-methylpropane-1,3-diol, TsOH, 4 Å molecule sieves; c) 5-amino-1-pentanol, TsOH; d) 4-amino-2-methyl-phenol, TsOH; e) N-(4-Aminophenyl)maleimide, TiCl₄, CH₂Cl₂.
Figure 7:
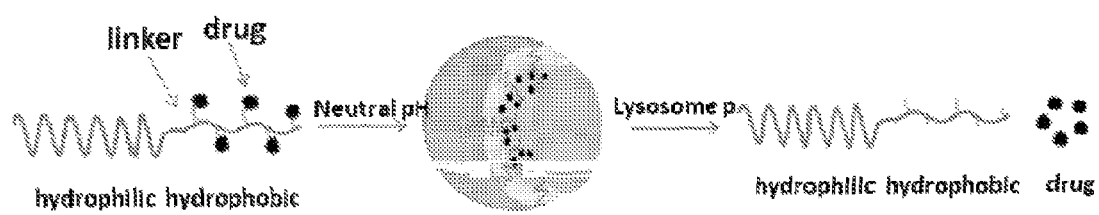
FIG. 7 illustrates the formation of a pH-sensitive micelle formulation disclosed herein and drug release.

Prodrug (6) provided a linkage with excellent chemical stability at neutral pH (e.g. the half-life for hydrolysis, $t_{1/2}$ (pH 7.4), is far more than 90 hrs) and fast conversion to beta-lap at acidic pH (e.g. $t_{1/2}$ (pH5.0)=1.1 hrs). A pH-sensitive copolymer, methoxy-terminated poly(ethylene glycol)-b-poly(diisopropylaminoethyl methacrylate-co-(2-(2-pyridyldisulfide) ethylmethacrylate) (mPEG$_{114}$-b-P(DPA$_{15}$-co-PDMS$_3$) copolymer was synthesized (see Example 6), and beta-Lap was conjugated via thiol-maleimide linkage. The resulting copolymer formed beta-lap-conjugated micelles by a solvent evaporation method. The micelles were spherical in shape by transmission electron microscopy analysis with a hydrodynamic diameter of 21 nm by dynamic light scattering analysis. Drug release studies showed that beta-lap release was highly pH dependent, with 3.3±0.5% and 60.3±2.6% of β-lap released from micelles at pH 7.4 and pH 5.0 in 72 hours, respectively. The loading efficiency reached 7.4% by weight, 8 times higher than by encapsulation method. A release study showed the polymeric micelles very slowly release β-Lap in neutral pH, however, in acidic condition fast release was observed (FIG. 4). In vitro evaluation of the polymeric micelles on cell cytotoxicity to A549 lung cancer cell lines exhibited similar NQO1-dependent toxicity as β-lap and β-lap was the effective component of the micelles. These results demonstrated the usefulness of dual pH-sensitive β-lap-conjugated micelles as an effective therapeutic strategy against NQO1-overexpressing tumor cells.

Preparation and Characterization of β-Lap Prodrug Conjugated Micelles

β-lap prodrug conjugated micelles were prepared according to a previously published procedure (Elvin Blanco, E. A. B., Ying Dong, Brent D. Weinberg, Damon M. Sutton, David A. Boothman, Jinming Gao. (2007) β-Lapachone-containing PEG-PLA polymer micelles as novel nanotherapeutics against NQO1-overexpressing tumor cells. J. Controlled. Release 122, 365-374). Briefly, mPEG$_{114}$-b-P(DPA$_{15}$-co-PDMS (6)$_3$) was dissolved in DMF and added drop-wise into 10 mL of distilled water under ultrasonication. The micelle solution was then ultrafiltrated for more than 6 times to remove DMF using the centrifugal filter (Millipore, MWCO 3,000). The final concentration of β-lap prodrug was adjusted to 2 mmol/mL.

The morphology of the micelles at pH 7.4 and 5.0 were observed on a JEOL 1200EX II transmission electron microscopy (TEM). Samples (1 mg/mL) were placed on a carbon-coated copper grid and negatively stained with 2% phosphotungstic acid. The particle size and distribution of micelles were determined by dynamic light scattering analysis (DLS, Malvern Zetasizer Nano-ZS) with 633 nm laser at 25° C. and at a scattering angle of 173°. The number-weighted mean value was obtained from triplicate samples. β-lap content in micelles was also determined by disintegration of micelles in pH 1.0 HCl aqueous solution and analyzed by HPLC method.

At pH 7.4, TEM imaging indicated the micelles were spherical particles with a clear margin (FIG. 2a), and the size of micelles were about 25±6 nm. At pH 5.0 all the micelles collapsed or disappeared (FIG. 2b), and the dynamic size was about 21 nm by number (FIG. 2c), which was consistent with TEM result. The intensity of light scattering was low at pH 5.0. The size variation indicated the polymeric micelles were integral spherical particles under neutral pH, and dissembled under acidic conditions.

Drug Conversion and HPLC Analysis.

For β-lap conversion study, prodrug (6) was dissolved in acetonitrile/buffered solutions (30:70, v/v) with different pH values (pH 7.4, 6.5, and 5.0) and adjusted to 5 μmol/mL. Prodrug (6) solutions were incubated at room temperature. At predetermined time points, 20 μL of the prodrug (6) solution was injected into HPLC to analyze prodrug (6) and β-lap simultaneously. The HPLC system consisted of a quaternary pump, a vacuum degasser, an autosampler, a C18 column (4.6 mm×250 mm, Agilent, CA) and UV detector at 254 nm (Perkin Elmer, MA, USA). The mobile phase was acetonitrile/water (60:40) and a flow rate of 1.0 mL/min was used. Prodrug (6) and β-lap concentration in the samples were obtained from calibration curves.

FIG. 1 shows conversion of prodrug (6) into β-Lap at different pH. FIG. 1a shows HPLC detection of prodrug (6) conversion at 5, 90, and 600 mins at pH 5.0. FIG. 1b shows quantitative analysis of prodrug (6) conversion at pH 5.0, showing both the decrease of prodrug (6) and formation of β-lap. FIG. 1c shows a comparison of β-lap formation from prodrug (6) at pH 5.0, 6.5 and 7.4.

This imine prodrug (6) proved to be more sensitive to acid and stable in neutral pH (FIG. 1). HPLC analysis of prodrug (6) hydrolysis showed that at 5 mins in pH 5.0 buffer only a trace of β-Lap (5 min peak) and Mal linker (3.5 min peak) was released, and most of prodrug (6) (11 min peak) was integral. After 1.5 hr the peaks of β-Lap and Mal linker were greatly improved, the prodrug (6) peak was significantly decreased; more than 50% of prodrug (6) was converted into β-Lap. After 10 hrs only Mal linker and β-Lap peak exist, all prodrug (6) was hydrolyzed (FIG. 1-a). Hydrolysis of prodrug (6) and accumulation of β-Lap were determined at different time points on HPLC; the half life of prodrug (6) converted into β-Lap was about 1.1 hrs (FIG. 1-b). Cumulative conversion of β-Lap at different time points at pH 7.4, 6.5 and 5.0 were determined. At pH 6.5 after 24 hrs about 30% prodrug (6) was converted into β-Lap, at pH 7.4 after 24 hrs about only 3.3% prodrug (6) was converted into n-Lap. The release of β-Lap at acidic condition is much faster than at neutral pH (FIG. 1-c). The hydrolysis profile of prodrug (6) indicated that this β-Lap prodrug is useful for pH sensitive drug release.

Without wishing to be bound by theory, the fast release of beta-lap at pH 5.0, and slow release at pH 7.4 may be due to the electron withdrawing effect at two sides of the C=N bond. Upon exposure of the molecule to acidic conditions, protonation of the C=N bond can readily break the balance of electron effect.

In Vitro Drug Release Study

To determine release kinetics of n-lap conjugated micelles, 1 mL of micelles was added into Spectrum Float-A-Lyzer dialysis devices (Fisher Scientific Inc., MWCO 8-10 k) and dialyzed against 6 mL of acetate buffer (pH 5.0) or phosphate buffer (pH 7.4) at 37° C. with gentle shaking (Alani, A. W. G., Bae, Y., Rao, D. A., and Kwon, G. S. (2010) Polymeric micelles for the pH-dependent controlled, continuous low dose release of paclitaxel. Biomaterials 31, 1765-1772). At designated time point, 1 mL of release medium was sampled and replaced with an equal amount of fresh buffer solution to ensure sink condition. The released 3-lap from micelles was determined by UV-Vis spectrometer at 257 nm. The error bars were obtained from triplicate samples.

Figure 2:
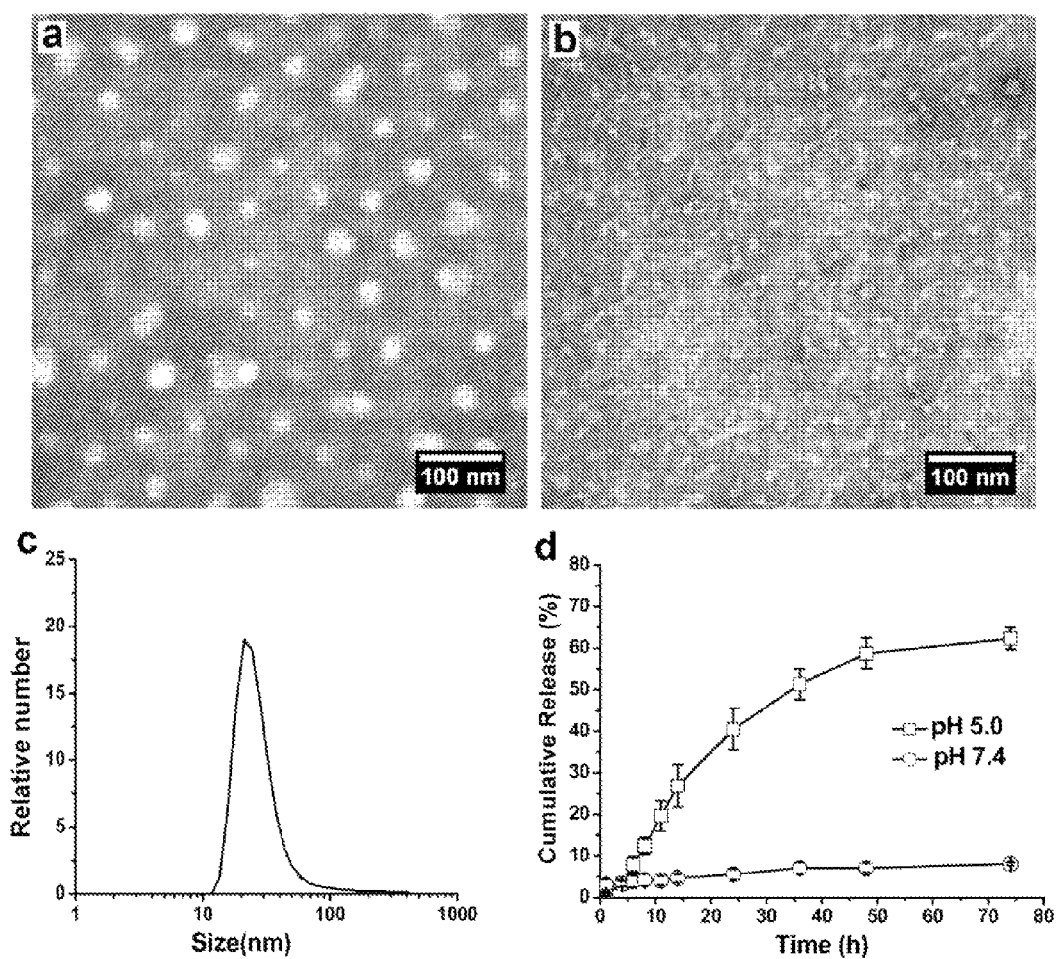
FIG. 2a is a TEM image of prodrug (6)-conjugated micelles at pH 7.4.
FIG. 2b is a TEM image of prodrug (6)-conjugated micelles at pH 5.0.
FIG. 2c shows particle size and distribution of prodrug (6)-conjugated micelles at pH 7.4.
FIG. 2d shows cumulative release of β-lap from prodrug (6)-conjugated micelles at pH 7.4 and 5.0 at 37° C.

The release of β-Lap from polymer mPEG-b-P(DPA-co-PDMS (6)) micelles was evaluated at pH 7.4 and 5.0 over 72 hrs by dialysis method in Float-A-Lyzer. In the hydrolysis process, β-Lap was released continuously from the polymeric micelles, no burst release was observed. At pH 5.0, in the first 12 hours, the release speed of β-Lap showed acceleration tendency, after that the release speed was reduced (FIG. 2d). At pH 7.4, only slight β-Lap was released in 72 hrs. The ratio of β-Lap released from micelles after 72 hrs at pH 5.0 and 7.4 were 60.3±2.6% and 3.3±0.5% (FIG. 2d), respectively. The observed release of β-Lap did not reached 100% because the absorption of β-Lap on the cellulose membrane of the Float-A-Lyzer. This demonstrated that β-Lap was released from polymeric micelles at pH 5.0, whereas at pH 7.4 the polymeric micelles maintain integrity, and β-lap is not released.

Cytotoxicity Assays

Long-term, relative survival was assessed based on DNA content as described (Pink, J. J., Planchon, S. M., Tagliarino, C., Varnes, M. E., Siegel, D., and Boothman, D. A. (2000) NAD(P)H:Quinone oxidoreductase activity is the principal determinant of beta-lapachone cytotoxicity. J. Biol. Chem. 275, 5416-24). Briefly, A549 cells were seeded at $5 \times 10^3$/well in 48-well dishes a day before experiments. Cells were then mock-treated or exposed to various doses of β-lap or β-lap prodrug (6) conjugated micelles for preferred time in the presence or absence of dicoumoral (40 μM) as indicated. Subsequently, cells were replenished with drug-free medium and allowed to grow for 5-7 days until control cells reached ~100% confluence. DNA content was determined by Hoechst 33258 staining and fluorescence detection using a plate reader (Perkin-Elmer, Boston, Mass.). Results were graphed as means±SE from sixtuplicate. Independent experiments were repeated at least three times. DIC is a specific NQO1 inhibitor and used to block β-Lap induced cytotoxicity.

Micelles Induced NQO1-Mediated Toxicity in A549 NSCLC Cells.

Figure 3:
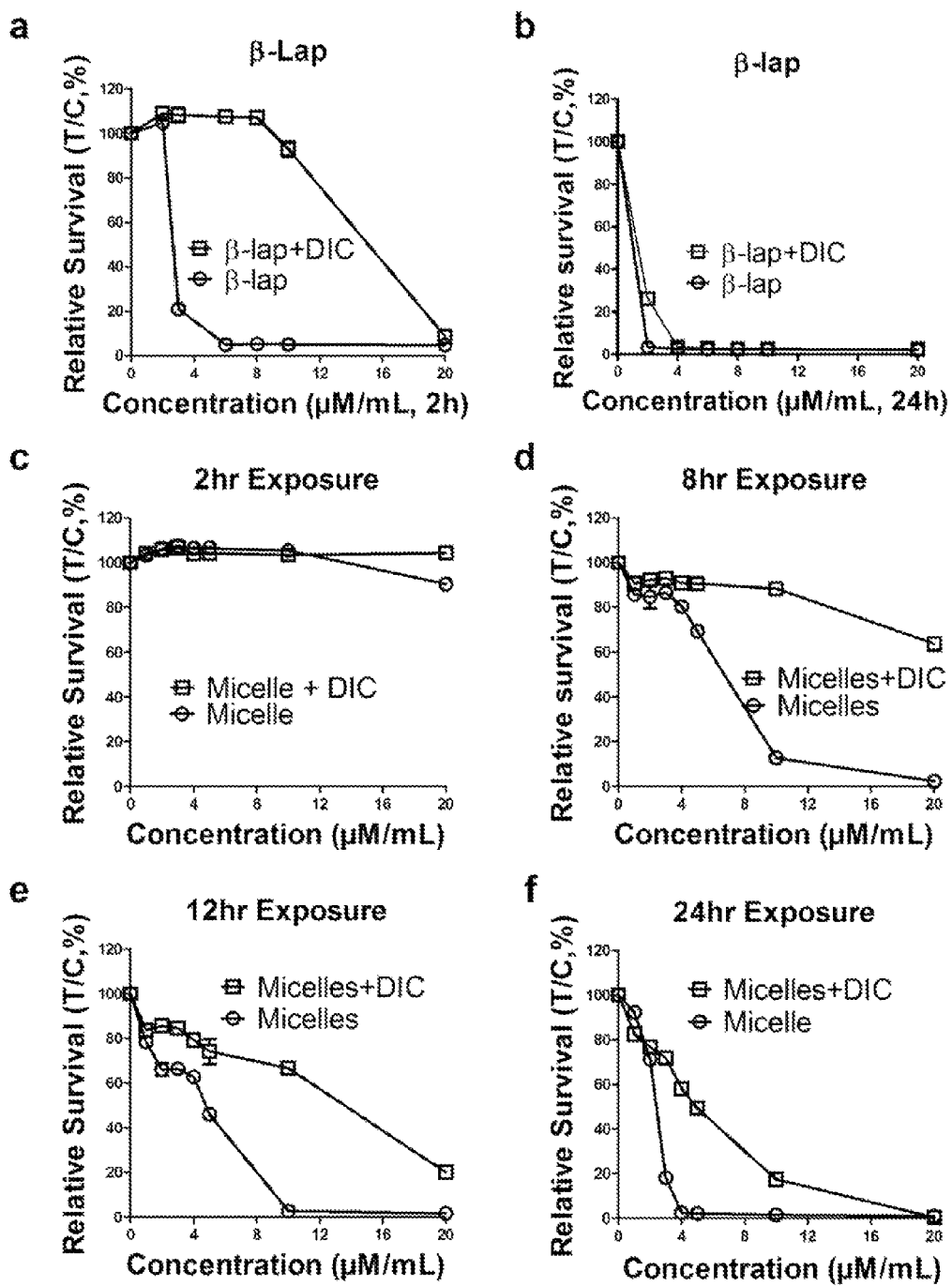
FIG. 3 shows cytotoxicity of prodrug (6)-conjugated micelles in human lung cancer A549 Cells.

Numerous studies (Bey, E. A., Bentle, M. S., Reinicke, K. E., Dong, Y., Yang, C. R., Girard, L., Minna, J. D., Bornmann, W. G., Gao, J., and Boothman, D. A. (2007) An NQO1- and PARP-1-mediated cell death pathway induced in non-small-cell lung cancer cells by beta-lapachone. Proc. Natl. Acad. Sci. USA 104, 11832-11837) have shown that ~2 h exposure to lethal doses of β-lap is sufficient to reach maximal cytotoxicity in different types of tumors. FIG. 3a shows 5 μMol/L of β-lap was sufficient to reach maximal cytotoxicity for A549 cells within 2 hours. Compared to β-lap, micelle particles showed poor toxicity at a dose of up to 20 μM after 2 h treatment (FIG. 3c). However, with prolonged incubation time, micelle toxicity started to be noticed in both dose- and time-dependent manner (FIGS. 3d-f). 20 μM of micelle led to 90% of cell death after 4 h exposure (not shown) while 10 μM of micelle appeared to be $LD_{90}$ after 8 h exposure (FIG. 3d). 5 μM of micelle shifted from $LD_{30}$ at 8 h treatment (FIG. 3d) to $LD_{50}$ at 12 h treatment (FIG. 3e). Massive cell death occurred after 24 h exposure of micelle even at a concentration of 3 μM (FIG. 3f). No toxicity was observed after treatment with polymer or linker only up to 24 h (not shown) suggesting that the toxicity indeed came from β-lap component of the micelle particles. Importantly, dicoumarol, a specific NQO1 inhibitor, blocked micelle-induced cytotoxicity as found in β-lap-induced cytotoxicity further confirming that the cell death seen in A549 cells after micelles treatment was caused by encapsulated β-lap in the micelle particles. Similar to β-lap, the therapeutic window of micelle particles started to close with a continuous treatment of 24 h period (FIGS. 3b and 3f).

The in vitro cell cytotoxicity study showed that micelles possessed similar NQO1-dependent toxicity as β-lap alone, besides the shift of toxic doses to a higher range. This indicated that the effective component of the micelles is β-lap.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound comprising a polymer conjugated with a pH-sensitive prodrug of beta-lapachone, wherein the compound is capable of forming a micelle, and wherein the pH-sensitive prodrug further defined by the formulas:

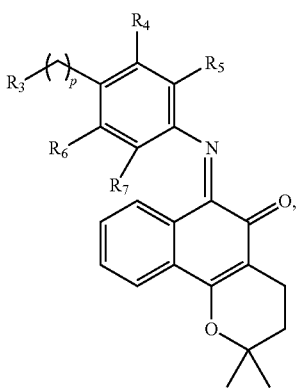

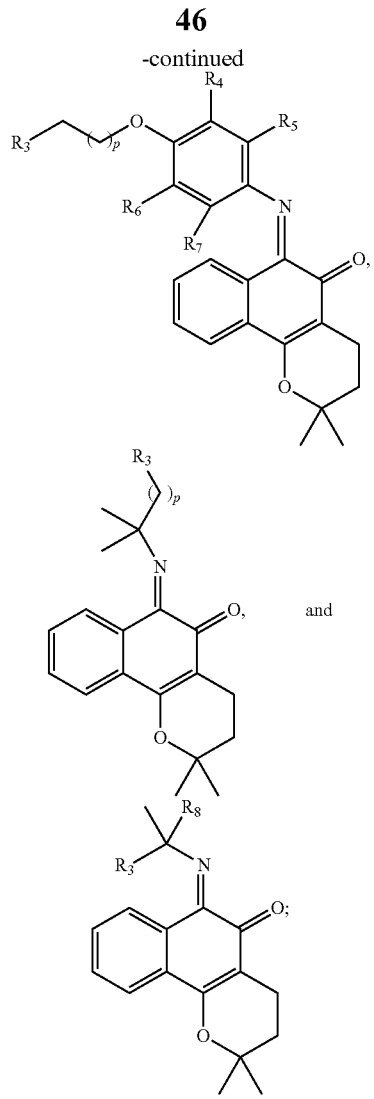

wherein
$R_8$ is a side chain of a D or L amino acid other than —H;
$R_3$ is —NH$_2$, —OH, —SH, or

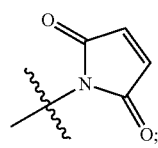 [SMILES: *N1C(=O)C=CC1=O]

each of $R_4$, $R_5$, $R_6$, and $R_7$ is independently —H, —X, —OCH$_3$, or —CH$_3$;
X is a halogen; and
p is an integer between 0 and 20.

2. The compound of claim 1, wherein $R_8$ is —CH$_3$.

3. The compound of claim 1, wherein $R_3$ is

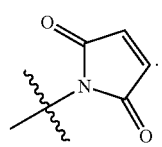

4. The compound of claim 1, wherein $R_3$ is —OH.

5. The compound of claim 1, wherein each of $R_4$, $R_5$, $R_6$, and $R_7$ is H.

6. The compound of claim 1, wherein X is Cl, Br, I, or F.

7. The compound of claim 1, wherein p is 0-6.

8. The compound of claim 1, wherein the prodrug is

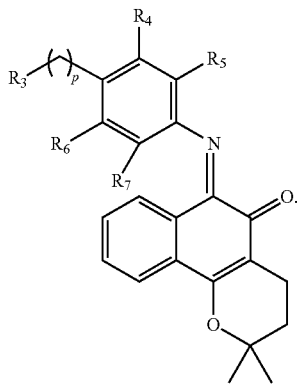

9. The compound of claim 1, wherein the prodrug is

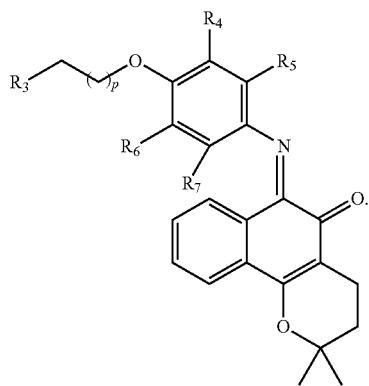

10. The compound of claim 1, prodrug is

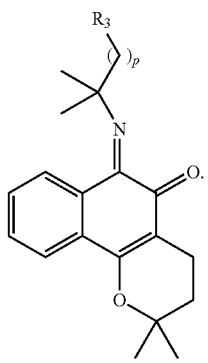

11. The compound of claim 1, wherein the prodrug is Malpil.

12. The compound of claim 1, wherein the prodrug is Eapil.

13. The compound of claim 1, wherein the compound comprises a pH-sensitivie linker, and wherein the pH-sensitive linker is sensitive to a pH between about 5.0 and about 7.4.

14. The compound of claim 13, wherein the prodrug is linked to the polymer by a bond selected from the group consisting of: an ester bond, an amide bond, a disulfide bond, or a thioether bond.

15. The compound of claim 1, wherein the polymer comprises a block copolymer comprising a hydrophilic polymer segment and a hydrophobic polymer segment.

16. The compound of claim 15, wherein the polymer comprises a pH responsive segment.

17. The compound of claim 16, wherein the hydrophobic polymer segment is the pH responsive segment.

18. The compound of claim 15, wherein the hydrophilic polymer segment comprises polyethylene oxide (PEO).

19. The compound of claim 1, comprising a block copolymer comprising a hydrophilic polymer segment and a hydrophobic polymer segment,
wherein the hydrophilic polymer segment comprises a polymer selected from the group consisting of: poly(ethylene oxide) (PEO), poly(methacrylate phosphatidyl choline) (MPC), and polyvinylpyrrolidone (PVP),
wherein the hydrophobic polymer segment comprises:

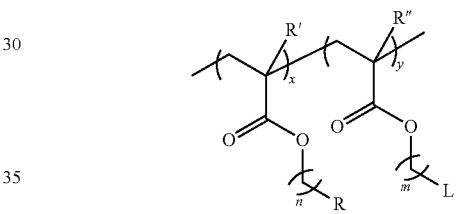

wherein R' is —H or —CH$_3$,
wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring,
wherein n is 1 to about 10,
wherein x is about 10 to about 50 in total,
wherein L is the prodrug conjugated to the polymer by a linker moiety,
wherein y is 1 to about 30,
wherein R" is —H or —CH$_3$;
wherein m is 1 to about 10; and
wherein the moieties comprising R and the moieties comprising L may be arranged in any order.

20. The compound of claim 19, comprising a compound of Formula I:

(Formula I)

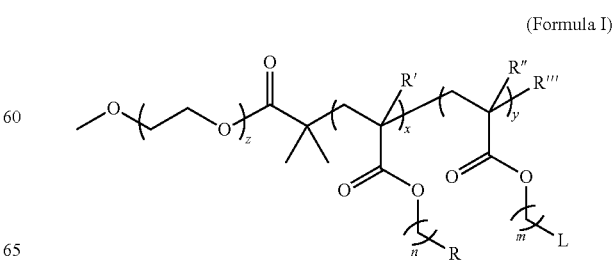

wherein z is such that the PEO is about 2 kD to about 20 kD in size, wherein R''' is any suitable moiety, and wherein the following portion of the structure:

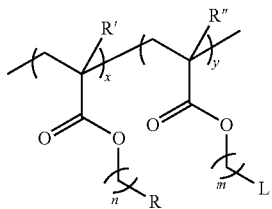

may be arranged in any order.

21. The compound of claim 20, wherein z is about 114.

22. The compound of claim 20, wherein R''' is an end group resulting from a polymerization reaction.

23. The compound of claim 19, wherein the following portion of the structure:

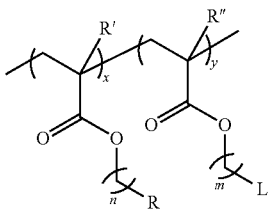

is randomized.

24. A composition comprising a pH-sensitive micelle, wherein the pH-sensitive micelle comprises a compound according to claim 19.

25. The composition of claim 24, wherein the micelle has a pH transition range of less than about 1 pH unit.

26. The composition of claim 24, wherein the micelle has a pH transition value of about 5 to about 8.

27. A composition comprising a micelle, wherein the micelle comprises a compound of claim 1.

28. The composition of claim 27, wherein the micelle is stable at a neutral pH and releases beta-lapachone at a physiologically acidic pH.

29. A method for treating breast, colon, lung, pancreatic, or prostate cancer in an individual in need thereof, comprising administration of an effective amount of a composition of claim 27 to the individual.

* * * * *

UNITED STATES PATENT AND TRADEMARK OFFICE
CERTIFICATE OF CORRECTION

PATENT NO.        : 9,631,041 B2                                  Page 1 of 1
APPLICATION NO.   : 13/825524
DATED             : April 25, 2017
INVENTOR(S)       : Jinming Gao et al.

It is certified that error appears in the above-identified patent and that said Letters Patent is hereby corrected as shown below:

In the Claims

In Claim 10, Column 47, Line 45, after "claim 1," insert --wherein the--.

In Claim 13, Column 48, Line 2, delete "sensitivie" and insert --sensitive-- therefor.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO.         : 9,631,041 B2
APPLICATION NO.    : 13/825524
DATED              : April 25, 2017
INVENTOR(S)        : Jinming Gao et al.

Page 1 of 1

It is certified that error appears in the above-identified patent and that said Letters Patent is hereby corrected as shown below:

In the Specification

In Column 1, Lines 16-21 delete paragraph and insert:
--This invention was made with government support under grant numbers CA102792 awarded by The National Institutes of Health, and W81XWH-06-1-0198 W81XWH-05-1-0248 W81XWH-04-1-0301 awarded by the Department of Defense. The government has certain rights in the invention.-- therefor.

Signed and Sealed this
Seventh Day of July, 2020

Andrei Iancu
*Director of the United States Patent and Trademark Office*